United States Patent [19]

Wrasidlo et al.

[11] Patent Number: 4,937,196
[45] Date of Patent: Jun. 26, 1990

[54] MEMBRANE BIOREACTOR SYSTEM

[75] Inventors: Wolfgang J. Wrasidlo, LaJolla; Frieder K. Hofmann, Oceanside; Dirk M. deWinter, Vista, all of Calif.

[73] Assignee: Brunswick Corporation, Skokie, Ill.

[21] Appl. No.: 395,655

[22] Filed: Aug. 18, 1989

[51] Int. Cl.$^5$ ............................................. C12M 1/04
[52] U.S. Cl. ................................... 435/313; 435/284; 435/287; 435/310
[58] Field of Search ............... 435/313, 310, 284, 287, 435/240.242, 286

[56] References Cited

U.S. PATENT DOCUMENTS

| | | |
|---|---|---|
| 3,489,647 | 1/1970 | Kolobom . |
| 3,734,851 | 5/1973 | Matsumura . |
| 3,809,613 | 5/1974 | Vieth et al. . |
| 3,948,732 | 4/1976 | Haddad et al. . |
| 4,087,327 | 5/1978 | Feder et al. . |
| 4,201,845 | 5/1980 | Feder et al. . |
| 4,220,725 | 9/1980 | Knazek et al. ............... 435/240.242 |
| 4,225,671 | 9/1980 | Puchinger et al. . |
| 4,241,187 | 12/1980 | White ................................. 435/284 |
| 4,391,912 | 7/1983 | Yoshida et al. ..................... 435/241 |
| 4,537,860 | 8/1985 | Tolbert et al. .................. 435/287 X |
| 4,661,455 | 4/1987 | Hubbard . |
| 4,661,458 | 4/1987 | Berry et al. . |
| 4,689,301 | 8/1987 | Adet et al. ......................... 435/284 |
| 4,693,983 | 9/1987 | Davies et al. ...................... 435/284 |
| 4,720,462 | 1/1988 | Rosenson . |
| 4,804,628 | 2/1989 | Cracaner et al. ............... 435/310 X |

FOREIGN PATENT DOCUMENTS

| | | |
|---|---|---|
| 39875 | 9/1981 | Japan . |
| 256375 | 12/1985 | Japan . |
| 2178447 | 2/1987 | United Kingdom . |

OTHER PUBLICATIONS

Biotechnology and Bioengineering, vol. XXIII, pp. 79–95 (1981), (K. Ku et al.), "Development of a Hollow-Fiber System for Large-Scale Culture of Mammalian Cells", see pp. 83–94.

Primary Examiner—Larry Jones
Attorney, Agent, or Firm—Waldron & Associates

[57] ABSTRACT

A bioreactor is disclosed in which cells are confined to a compartment formed by porous hydrophyllic sheet membranes through which a nutrient solution diffuses in and exocellular products and metabolic waste diffuse out. Adjacent gas compartments allow the flow of free oxygen into the cell compartment. Each cell compartment is configured to place cells within about 100–200 micrometers of the oxygen transport membrane.

25 Claims, 9 Drawing Sheets

MEMBRANE BIOREACTOR SYSTEM

This application is a continuation of applicant's copending application, Ser. No. 07/068,203, filed Jun. 30, 1987, now abandoned benefit of which is hereby claimed under 35 U.S.C. 120.

BACKGROUND OF THE INVENTION

This invention relates to bioreactors which can be used to enable cells to produce cell products, and particularly to enable hybridomas to produce monoclonal antibodies.

The bioreactor system resembles a living organism in many ways. It has an enclosure in which cells can live, multiply, and produce; a circulating system for supplying water and nutrient and removing waste from the cells; a respiratory system for providing oxygen and removing carbon dioxide; and means for removing cell products and wastes from the system. The success of the whole system depends not only on how well each of the elements is designed but even more on how well they interact and coordinate with each other to maintain effective conditions for the production of cell products.

Advances in biomedical technologies have initiated a demand for mammalian cell products. The diagnostic, prophylactic, and therapeutic applications for such cell products appear vast and an ever-expanding variety of possibilities will generate new markets far into the future. The exploding demand for mammalian cell products has spurred considerable research into mass cell culture techniques and bioreactors.

Currently, several bioreactor designs have been developed, used and marketed by adapting existing devices for use in the realm of mammalian cell culture. The two technologies most commonly exploited in this fashion are those of bacterial fermenters (batch culture), and hollow fiber dialysis units modified for stationary cell culture. Each system brings with it certain inherent advantages, but there are also certain limitations and disadvantages with regard to mammalian cell culture.

Bulk fermentation in batch operations is limited by the absence or great difficulty of the removal of cell products, and particularly toxic materials and other materials which inhibit cell metabolism or the production of certain cellular products. In addition, conditions of bulk fermentation are generally based on air or oxygen spargers to provide for the oxygen requirements of the cells, which makes for excessively turbulent conditions within the reactor. Sterility in large fermentation tanks is a difficult problem, and when contamination occurs, the losses in considerable labor and production time and the expensive materials when the batch is dumped cn be quite large.

Various considerations have made immobilized cell bioreactors preferable over alternative systems for the commercial production of monoclonal antibodies as well a other mammalian cell products. Immobilized hybridoma cells in particular can produce their products virtually indefinitely in such bioreactors without disturbances related to the harvesting of products. However, adequate oxygenation of the cultured cells and removal of carbon dioxide has been a limiting factor in the development of efficient and economical designs.

Most immobilized-cell bioreactor designs in the prior art deliver oxygen dissolved in the nutrient medium to the cells and remove carbon dioxide as it dissolves in the same medium. Since oxygen is rapidly depleted, large volumes of nutrient medium must be circulated through the bioreactor to meet cellular needs. The flow rates based on oxygen consumption are generally adequate for waste removal. The large volumes of circulating nutrient medium necessary for scaled-up producton bioreactors of this kind require large pumps which are expensive and greatly increase the size of the bioreactor unit. High nutrient medium flow rates also increase fluid pressure and turbulence in the system, with the concurrent risk of substantial losses of both production cells and of relatively expensive nutrient components through the physical stresses imposed, particularly high shear conditions.

A diverse variety of approaches have been employed in the development of membrane based cellular bioreactors. See for example the varying approaches illustrated in U.S. Pat. Nos. 3,997,396, 4,087,327, 4,201,845, and 4,537,860.

In 3,997,396, attachment dependent cells are attached on the outer surface of hollow fiber membranes, and derive their oxygen supply from an air or other oxygen carrier flowing on the inside of the fiber. In this approach, the number of cells is limited to a monolayer on the available membrane surface, limiting the cell density to low levels. In addition, with pure oxygen, most cells are limited in their ability to survive the high oxygen tensions. If the applied gas pressure is too high, it may produce gas bubbles that will disrupt the cells or their attachment. On the other hand, the requirement that the cells attach to the surfaces requires that the membrane be hydrophilic, and thus susceptible to wetting by the nutrient, and passage of materials into and even through the pores, causing clogging and disruption of the flow. This will dictate a high gas pressure to limit the rate of these phenomena, and damage to the cells will inevitably result.

A different approach is taught in 4,087,327; in this patent it appears that the outer surfaces of hollow fiber membranes or solid fibers are used as attachment sites for attachment dependent cells, but the interior of the fibers, when hollow fibers are employed, does not appear to be used. Oxygen is apparently transported to the cells dissolved in the nutrient. The nutrient is pumped by pressure transversely through the cell chamber, subjecting the cells to undesirable pressure and flow turbulence which can damage the cells.

U.S. Pat. No. 4,201,845 is a Continuation-in-Part of 4,087,327, supra. In this version, the interior of hollow fiber membranes are used for oxygen transport into the cell reaction zone. The nutrient is again pumped transversely through the cell chamber, with the attendant problems. The difficulties with this teaching are the same as those noted above with respect to 3,997,396.

U.S. Pat. No. 4,537,860 teaches a cell reactor which employs an annular construction of porous cylinders of polymer or ceramic materials to confine cells, pump nutrient through the cell chamber (with all the attendant difficulties of through flow operations), and semipermeable, silicone rubber tubing to carry gas into, and to cause it to perfuse into, the cell chamber. The distance of the cells can be as much as 1 to 2 cm from the oxygen supply tube, and coupled with the properties of the silicone rubber tubing, leads to the requirement that the oxygen source be fed under such pressure that the supply tube passes gaseous phase into the reaction zone in order to provide adequately oxygen to the cell chamber, with attendant turbulence, high internal pressures and damage to the cells. This "sparger" approach leads to inadequate rates of oxygen uptake to assure cell producivity and even viability in substantial parts of the vessel.

OBJECTS OF THE INVENTION

It is an object of this invention to provide a bioreactor which can be used to enable cells to produce cell products.

It is another object of this invention to provide a bioreactor which is a mammalian cell bioreactor.

It is also an object of this invention to provide a biorector which is a hybridoma bioreactor.

It is an object of this invention to provide a bioreactor which minimizes cell stress by enclosing the cells between microporous membranes in a reactor zone.

It is another object of this invention to provide a bioreactor which provides a large membrane surface area.

It is yet another object of this invention to provide a bioreactor which includes a continuous feed supply and continuous bleed system.

It is a further object of this invention to provide a bioreactor in which the cells of the bioreactor are not removed from the reactor zone with the nutrient medium.

It is yet a further object of this invention to provide a bioreactor which allows for the handling of small volumes of liquid nutrient medium.

It is an object of this invention to provide a bioreactor which allows for the conservation and recirculation of reusable or expensive nutrient medium components.

It is also an object of this invention to provide a bioreactor which includes temperature regulation by means of an in-line nutrient medium heating system.

It is another object of this invention to provide a bioreactor which can accommodate both attachment independent and attachement dependent cell lines.

It is yet another object of this invention to provide a bioreactor which consists of modular units such that several modular bioreactor units with either the same or different cell lines can be supplied by a single central nutrient supply.

It is a further object of this invention to provide a bioreactor which incorporates a separate gas exchange means so that oxygen is circulated through the bioreactor in the gaseous phase, as air or another gas mixture, rather than dissolved in the nutrient medium.

It is an object of this invention to provide a compact bioreactor which utilizes a minimum of space.

It is a further object of this invention to provide a bioreactor which facilitates product recovery by confining cells thus preventing the cells from being harvested during product recovery.

It is also an object of this invention to provide a bioreactor which maximizes productivity by effective nutrient and oxygen delivery and carbon dioxide and other waste removal.

It is also an object to provide for independent delivery of nutrient and oxygen such that the amounts of each is defined and controlled in relation to the cellular requirements for the production of the intended cell product.

It is yet another object of this invention to provide a bioreactor which optionally provides support for attachment dependent cells.

SUMMARY OF THE INVENTION

A bioreactor is an artificial environment for the growth of organisms. The bioreactor of the present invention is a continuous, integrated membrane bioreactor system which differs from the prior art bioreactor systsms is being designed from its inception as a hybridoma or mammaliam cell bioreactor. The ideal bioreactor would be a system which integrates productivity, economy, and versatility.

The bioreactor of the present invention meets the nutritional and physical needs of hybridomas or mammalian cells, allows for the hervesting of products, and maintains sterile integrity of the system by combining several individual apparatus having separate functions into an integrated, functioning unit.

The feed supply of the bioreactor assures the fulfillment of all cellular nutritional needs and the bleed or removal system removes wastes and products at any desired rate as appropriate for the culture. Nutrient medium bled from the circulation is passed through various steps to purify the antibody product. Removal of nutrient medium need not be constrained by cell growth rates since the cells of the bioreactor of the present invention are stationary and thus are not removed with the medium. Product recovery, therefore, does not interrupt production.

Economy of operation is designed into the bioreactor of the present invention. Central to this consideration is the compact size of the cell enclosure which is made possible by the high cell densities achieved in the layered membrane design and the continuous feed and bleed nutrient medium system which minimizes the nutrient medium volume inside the bioreactor. Maximized product output per unit of volume minimizes the space necessary to house the bioreactor.

The continuous feeding system for nutrient medium means that only small volumes of sterile liquids are handled. Likewise, continuous removal and concentration of product keep volumes small. This keeps costs and the possibility of contaminations at a minimum and maximizes ease of operation. Aseptic breaks in the nutrient medium flow maintain sterility and prevent cross contamination.

Depending upon the cell line in culture, the nutrient medium may contain expensive components. These can be conserved and recirculated in the bioreactor of the present invention through the employment of appropriate separatory and purification techniques, such as the inclusion of an ultrafiltration module in the bleed system. This module can also be used to concentrate the product in the nutrient medium before harvesting. Cells do not interfere with product collection since they are retained in the cell chambers by the microporous membranes.

In-line nutrient medium heating obviates the need for an enclosing environmental chamber or at least reduces the demands on an environmental chamber while the maintenance requirements and costs are low.

Very little labor is required, particularly once the bioreactor is functional, and the initial costs of construction are very low compared to bulk fermentation batch devices. These are all aspects of an economical bioreactor design.

The bioreactor of the present invention is a very versatile design which will support all types of cells producing all types of products. Both attachment independent and dependent cell lines are suitable for the layered membrane design, particularly hybridomas. All the materials employed in such reactors, including nutrients, products, and cellular waste, including proteins, lipids, sugars, salts, organic and inorganic constituents, and simple and complex products, particularly monoclonal antibodies, are all compatible with this bioreactor design. The residence time of the product is variable and can be adjusted to the needs of the specific cell line. Toxic, inhibitory, or unstable products can be removed rapidly. Stable, non-interfering products may remain in the system for a time and be concentrated prior to removal.

The modular construction of each bioreactor unit and the ability of one nutrient medium preparation center to supply many bioreactors makes the bioreactor of the present invention adaptable to the production needs of any facility.

The entire bioreactor is compact.

While many bioreactor designs have specific advantages, the bioreactor of the present invention integrates advantageous design features for every aspect of hybridoma or mammaliam cell culture into a single integrated bioreactor unit. This unit is economical to operate, can be easily adapted to all cell line and product specifications and maximizes production.

In the bioreactor core of the present invention, the cells are confined between two membranes which form a cell chamber, at least one of which is microporous and hydrophilic and permits the free passage of all nutrients as well as monoclonal antibodies and other cell products. The nutrients medium does not have to carry dissolved gases, so the medium which returns to the reservoir is cycled back to the bioreactor without having to pass through a separate, external gas exchanger. Nutrient medium is continuously added to the system and product and waste are continuously withdrawn at the same rates.

The present invention includes several embodiments which solve the oxygen delivery and removal of carbon dioxide and other waste gases by incorporating a separate gas exchange compartment into an immobilized cell bioreactor thereby eliminating the need for a gas exchanger which is external to the bioreactor core. The central concept behind the design of these embodiments is that oxygen is passed through the bioreactor as air or another gas mixture, rather than dissolved in the nutrient medium. Oxygen diffuses directly into the cell space. The relatively high concentration of oxygen in air (or other appropriate gas mixture) as compared to that dissolved in the nutrient medium, and the low viscosity of gases as compared to liquids, allows a slow flow of air at low pressure to supply and abundance of oxygen to the cells. Similarly, excess carbon dioxide is more rapidly removed as a gas than dissolved in the nutrient medium. Nutrient medium can thus be circulated much more slowly, resulting in a smaller, more efficient and economical bioreactor.

The simplest embodiment interleaves a hydrophobic, microporous, membrane-bounded air chamber between two cell chambers in a layered membrane bioreactor. The cells are placed between a microporous hydrophilic membrane which separates them from the circulating nutrient medium and another, ultraporous membrane, this one hydrophobic, and separating them from a stream of appropriate gas. A mixture of air with about 5% of carbon dioxide seems desirable for most mammaliam cell lines. Appropriate hydrophobic membranes of polysulfone, teflon or polypropylene are available commercially.

In another embodiment, which is a variation of the simplest embodiment, a spacer screen is combined with or, alternatively, replaced with particulate support material for attachment dependent cells.

Any of these embodiments can be incorporated into either stacks of flat membranes or into a spiral-wound membrane format. The spiral can be formed in either an end-wound format or a center-wound format. Either configuration offers the advantages of simplicity of construction, compactness, low stress or cells and membranes, and low material and fabrication costs. The entire reactor component, in either configuration, can be prepackaged, offering great convenience and ease of use.

Initial experiments utilizing a single unit of an embodiment of the present invention incorporating a compartmentalized gas exchange chamber resulted in a three-fold increase in monoclonal antibody production over that obtained with the same cells oxygenated through the nutrient medium. This confirms that compartmentalized gas chamber bioreactor embodiments are more efficient than medium-dissolved gas bioreactor embodiments and provide for maximal oxygen and carbon dioxide exchange with the cells. Delivery of oxygen and removal of excess carbon dioxide through compartmentalized gas exchange chambers decrease the volume of nutrient medium circulated and increase the available oxygen, thus providing significant advantages for the economic manufacture of cell products in bioreactors.

SUMMARY DESCRIPTION OF THE DRAWINGS

FIG. 9 is a cross-sectional schematic view of a spiral-wound bioreactor with a gas exchange chamber showing end-wound construction, the spacer screens in each chamber not shown for clarity.

FIG. 10 is a cross-sectional schematic view of a spiral-wound bioreactor with a gas exchange chamber showing center-wound construction, the spacer screens in each chamber not shown for clarity.

DETAILED DESCRIPTION OF THE INVENTION

Figure 1:
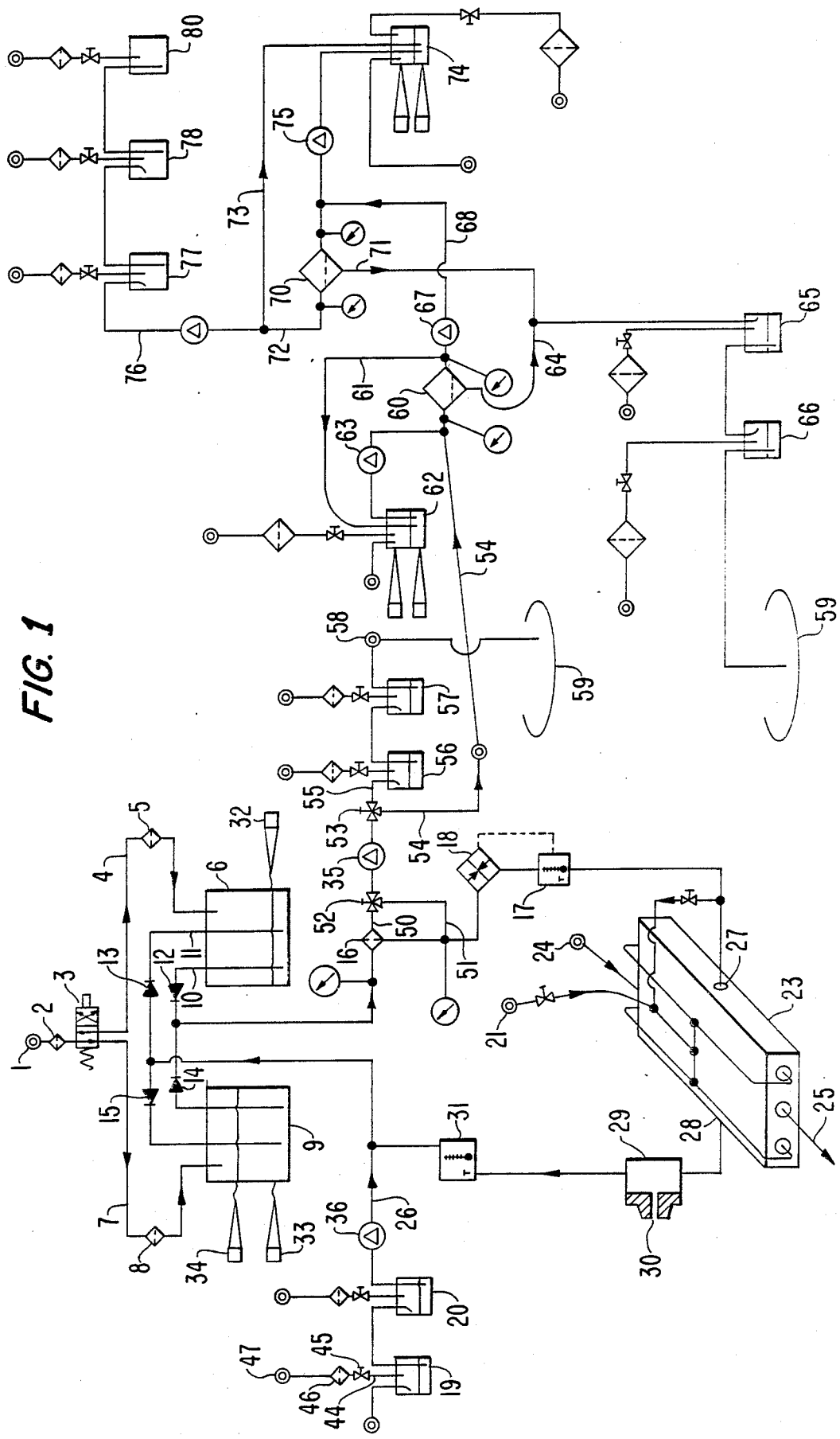
FIG. 1 is a flow diagram showing the bioreactor system of the present invention as a whole, and illustrating the configuration and operation of the various elements thereof.

Living cells have many complex growth and maintenance requirements. Survival of single celled organisms requires that they be very generalized in their functions. They must be able to find food, survive deprivation, and reproduce. The cells of a complex organism are very specialized and are unable to survive without the support of their sister cells which are specialized for other functions. They retain a limited ability to reproduce themselves but have no ability to survive lapses in nutritional or environmental support. The bases of bioreactor technology lie in the twin facts that cells can be chosen for their specific specialized functions, such as monoclonal antibody production, and that the nutritional needs of these cells can be met by artificial means. A bioreactor is a surrogate body for these artificially cultured cells and must therefore provide all of the services of a living body. The support systsms which must be provided by a bioreactor are easy to list, but the specifics of design and implementation encounter many subtle demands and restrictions, and offer myriad combinations of solutions of varying effectiveness.

First, the bioreactor must provide for the cells a physical enclosure which allows for proper growth and distribution, facilities uniform and consistent exposure to nutrients and oxygen, and effects rapid removal of cell products and wastes. Second, the bioreactor must provide a circulation system, or systems, which deliver nutients, growth factors and oxygen to the cells and carry away cell products and wastes.

The successful maintenance of mammalian cells in culture is only possible when a satisfactory environment is provided. This environment must stimulate the essential qualities of a complex living organism and thus might be expected to require a very complex apparatus. In fact, mammalian cells can be grown in simple glass or plastic dishes or bottles and a wide variety of other supports. This is possible as long as sterility is maintained, the cells are provided with sufficient oxygen and a nutrient medium at the proper pH and temperature, and wastes are removed.

Conditions which are merely adequate for cell growth, however, do not meet the demands for economical production of commercial quantities of cellular products such as monoclonal antibodies. Effective manufacturing by cells can only be achieved by maximizing efficiency and production.

A key factor for efficiency is the quantity of nutrient medium which must be handled to meed cellular needs. An examination of cellular requirements quickly reveals that the delivery of oxygen to the cells is the most critical parameter. This can be easily understood by considering an analogy with a living human who can survive days without water or weeks without food, but only minutes without oxygen. Cells in culture also die very rapidly without oxygen. Cells cultured in dishes, flasks, or bottles obtain their oxygen by diffusion from the air into the nutrient medium. This works, but is a slow process and limited to a small, laboratory scale. Two types of scaled-up cell culture systems have been developed, batch and immobilized cells. Batch systems are adaptations of bacterial fermenters. They require the handling of large volumes of sterile nutrient medium, have problems with shear forces disrupting cells, and in many designs must separate cells from media to harvest the product. Recolonization of large batches is also slow and expensive.

Most of the problems inherent in the batch system can be solved by using an immobilized cell system. Several versions of this type system are currently under development, including hollow fiber membranes, ceramic matrices, and the like. The common elements in these immobilized cells systems are that they eliminate shear problems by allowing for oxygenation without the necessity of vigorously agitating the nutrient medium in the presence of the cells and permit continuous collection of the cellular product from the nutrient medium without having to remove the cells. This continuous flow arrangement of the immobilized cell systems also makes much higher cell densities possible than does the batch process. Thus, the cells are not subjected to unhealthy physical forces and a smaller apparatus produces more product.

The physical support structure for the cells in the bioreactor of the present invention is any of a variety of layered membrane enclosures which combines to form the bioreactor core or cell enclosure. The various types of bioreactor core structures will be described in further detail below. The basic design for the bioreactor core integrates the gas exchanger into the same structure as the cell enclosure reactor zone. This design will be referred to herein as a compartmentalized gas exchange chamber or a direct aeration bioreactor. This system is analogous to the tracheal system of insects since there is direct diffusion of gases across a membrane separating cells and air. The liquid surrounding the cells cannot pass through the hydrophobic membrane into the gas chamber, and the pressure of the gas mixture must be slightly less than that of the nutrient medium to prevent bubble formation in the cell chamber.

In its most general form, the bioreactor of the present invention is made up of at least one reactor zone formed of porous sheet membranes, joined at their edges, which contains the cells.

One of the membranes is hydrophobilic, with a porosity suitable for the transport of nutrient into the reactor zone, and the transport of nutrient, cell products, and waste materials out of the zone. Nutrient is furnished to the reactor zone by diffusion through the hydrophilic membrane, at a rate suited to the cell metabolism, and preferably not much greater.

The other membrane is hydrophobic and ultraporous. The pore size of the hydrophobic membranes range from about 0.005 to 0.1 $\mu$m, preferably from about 0.01 to 0.05 $\mu$m. Oxygen, as such or more commonly in the form of air, and with possibly other additions, including minor amounts of carbon dioxide, for example, is supplied to the reactor zone through the membrane, where the oxygen diffuses into and through the nutrient and to the adjacent cells. If the pores are smaller than the low end of the above range, the pores restrict gas transport too much. On the other hand, if the pores are larger than the high end of the range, protein deposits and wetting agent constituents of the nutrient medium will gradually build up in the pores eventually allowing water and or nutrient medium to pass into the gas exchange chamber. Within the defined pore size range, depending on the specific constituents of the nutrient, proteins and the like will not cause wetting, and long term hydrophobic characteristics are achieved. The bioreactor core of this embodiment consists of membrane layers forming a nutrient medium chamber, a cell chamber, a gas exchange chamber, a cell chamber, a nutrient medium chamber, and so forth. Spacer screens are placed between the membrane layers; these serve to maintain proper spacing of the membranes.

In another embodiment, which is a variation of the simplest embodiment, the cell chamber spacer screen is replaced with very thin hollow fibers of hydrophobic material such as teflon or polypropylene, or the like, sealed at the ends. These hollow fibers perform the dual functions of maintaining proper spacing of membranes and increasing the surface area for gas diffusion. This occurs because gas will diffuse into and out of the fiber lumina from the adjacent air chamber much more rapidly than directly through the nutrient medium in the cell chamber. The greater efficiency of gas diffusion allows a wider cell chamber containing more cells, and thus higher production per unit size.

Another embodiment utilizes alternating cell and nutrient medium chambers enclosed by hydrophilic, microporous membranes, but replaces the cell chamber spacer screen with a layer of hydrophobic, microporous hollow fibers. These fibers pass completely through the cell chambers, are gathered into a manifold and carry a flow of air directly to the cell chambers.

The span between the two membranes is kept to a small, preferably uniform dimension to limit the distance required for the transport of oxygen from the hydrophobic membrane to the most remote cells. The span is preferably maintained by a separator. In preferred circumstances, the dimensions of the system are such that every cell is within 200 $\mu$m, preferably within about 100 $\mu$m, of the oxygen source, i.e., the surface of an oxygen transport membrane.

In its simplest configuration, there is a single reaction zone with a gas chamber on one side and a nutrient chamber on the other. In this configuration it will often be desirable to employ a plurality of reaction zone structures in a stack arrangement, each arranged with its membranes disposed in a face to face relationship with the corresponding membranes of its immediate neighbors. Thus, pairs of hydrophilic membranes alternate with pairs of hydrophobic membranes. The stacks are preferably all provided with appropriate separators, and are joined at their edges to form "media zones". The term media is used to encompass both nutrient and the oxygen supplies. The zone formed and bounded by the facing pair of adjacent hydrophilic membranes forms a nutrient supply chamber, and the zone formed by an adjacent facing pair of hydrophobic membranes constitutes an oxygen supply chamber. In such a stack, there is then established a repeating sequence of such zones, where every second zone is a cell chamber reactor zone, and each cell chamber is adjacent one oxygen supply chamber and one nutrient supply chamber.

Cell productivity in the bioreactor of the present invention is maximized by a number of features. The cells in the reactor zone provided between the enclosing microporous membranes are protected from shear forces generated by the circulating media. The cell chambers are filled through seeding and cell division to a density of approximately $10^9$ cell/cm$^3$ which approximates the cellular interactions of live tissue. This condition is congenial to the cells, and they will remain in the bioreactor and produce for extended periods. In the case of hybridomas or other so-called immortal cells, production can, in principle, continue indefinitely.

Production is enhanced by the very large membrane surface area separating the cell and media chambers which results in a highly efficient and uniform transfer of oxygen and nutrients to the cells.

Outside the reactor zone, in direct communication with the hydrophobic membrane, an oxygen supply means provides an oxygen supply to the reactor zone though the membrane, where it diffuses through the nutrient to the cells. The oxygen supply is most often air, or air with a small addition of carbon dioxide, although other oxygen containing gas streams may be employed as well.

Control of the nutrient supply is facilitate by particularly effective nutrient supply, make-up and pumping operations.

On the outside of the reactor zone, in direct communication with the hydrophilic membrane, there is a nutrient supply chamber, which provides a flow of nutrient across the face of the membrane. Nutrient diffuses into the reaction zone through the hydrophilic membrane, and nutrient, cell products and waste materials diffuse out of the reaction zone through the same membrane into the nutrient flow, and thus are carried out of the bioreactor. The nutrient stream is normally recirculated with processing to remove and recover the cellular products of interest and to eliminate the waste materials.

In pumping, the reactor is connected to a pair of reservoirs, which operate as a supply and receiver for the nutrient volume. Nutrient is fed from the supply to the reactor, and then to the receiver. As the supply is exhausted, and the receiver is filled, the operation is reversed, and the reactor is then supplied from the new supply. A system of check valves is used to direct the nutrient medium circulation which flows under the force of air pressure which is increased alternately above the medium in one of the two reservoirs. Sensors on the reservoirs detect the nutrient medium level and control the pressurizations. New nutrient medium is added intermittently or continuously to the recirculating volume. When the total circulation volume reaches a specific volume, as detected by sensors, a bleed pump begins operation. This pump ordinarily bleeds medium from the circulation slightly faster than nutrient medium is being added to the system. The bleed flow stream is treated to remove the intended cell product and waste materials, and the remaining nutrient can be eventually recirculated to the system. When the total circulation volume reaches another specific volume, as detected by sensors, the bleep pump stops operating.

A number of factors are primary in considering the design of a system to circulate the complete nutrient medium through the heater, gas exchanger, and cell enclosure or bioreactor core of the bioreactor. Reliability of all components should be maximized, minimal physical stress must be applied to the delicate nutrient medium, the flow should be unidirectional and all functions should be automatic. Component reliability is a critical factor to minimize necessary repairs, but more importantly because the failure of a component may jeopardize sterility or create environmental fluctuations in the bioreactor which are detrimental to cell productivity and survival.

The component most subject to failure in a bioreactor where nutrient medium must circulate is the pump. Diaphragm pumps are subject to diaphragm cracking. Peristaltic pumps suffer gear and tubing failures. These problems have been circumvented by using two nutrient medium reservoirs which can be pressurized with air and a system of check valves to direct the flow of nutrient medium. The check valves have an extremely long life expectancy. They have no breakable parts and the only moving part is the ball valve. Check valves also alleviate the undesirable qualities of pump action, such as cavitation, shear, and pulsation which can be detrimental to the medium and the cells. The compressor which pressurizes the nutrient medium reservoirs to drive the circulation is external to the circulation system, never touches the nutrient medium, and therefore measures can be taken to allow servicing or replacement without disruption of the bioreactor.

FIG. 1 is a diagram showing the nutrient medium circulation system for unidirectional flow through a cell enclosure with an external gas exchange unit. The same system can be used, without the external gas exchange unit, if the bioreactor core includes an internal gas exchange chamber.

Air to pressurize medium reservoirs 6 or 9 is pumped from inlet 1 through a 0.2 $\mu$m sterilizing filter 2 to a valve 3, which is a three-way vented solenoid, which directs it to either of the two reservoirs 6 or 9, via air lines 4 and 7. Additional filters of 0.2 $\mu$m pore size 5 and 8 are placed in the air lines 4 and 7 to assure sterile air enters the reservoirs. To demonstrate the circulation design, the present discussion will start with nutrient medium reservoir 6 filled with an appropriate amount of nutrient medium and being pressurized to initiate circulation.

As the pressure in nutrient medium reservoir 6 increases, nutrient medium is forced into two tubes 10 and 11, closing check valve 13 and opening check valve 12. The nutrient medium pressure then closes check valve 14 and the flow is thus directed through heater 18 and then through cell enclosure or bioreactor core 23 via inlet 27 and outlet 28. The media which exits the cell enclosure 23, passes through sampling site 29 with hypodermic access port 30, then through temperature monitor 31, and is directed through check valve 15 into nutrient medium reservoir 9. This flow continues until the level of the medium in nutrient medium reservoir 6 drops sensor 32.

At this point, sensor 32 sends a signal to air valve 3 which switches the air flow into nutrient medium reservoir 9 via line 7. The nutrient medium forced out of nutrient medium reservoir 9 closes check valve 15, opens check valve 14, closes check valve 12, follows the same route as before through heater 18 and cell enclosure 23, opens check valve 13 and enters nutrient medium reservoir 6. This flow pattern continues until sensor 33 detects the medium level, at which point sensor 33 sends a signal to air valve 3 which switches the air flow back into nutrient medium reservoir 6 and the cycle is again repeated.

Thus nutrient medium flow is unidirectional through the cell enclosure. Nutrient medium is also recirculated automatically simply by employing nutrient medium level sensors 32 and 33 to control the operation of the air pressure valve 3.

To minimize expense and bulk, the bioreactor of the present invention is not contained within an incubator for temperature regulation. Instead, the nutrient medium is passed through a regulated heater 18 which must maintain the nutrient medium at 37° C. However, at no time can the nutrient medium be subjected to temperatures much higher than this because of heat-sensitive components in the nutrient medium, and also to avoid corrosive processes such as sugar caramelization and mineral deposition which are results of excessive heat and would shorten the life of the bioreactor.

To meet these requirements, the heater is regulated by a thermistor 31 and heater control 17 which assures very precise, short period, intermittent, power-regulated heating pulses. This keeps the walls of the heater from getting excessively hot. The nutrient medium passes through the heater in very thin passages for maximum efficiency of heat transference. The heater is also positioned for a vertical medium flow so that any gas bubbles which may occur will pass rapidly through the heater and not cling to the sides where they would create hot spots. The thermistor for reactor temperature monitoring is located at the nutrient medium exit port of the cell enclosure.

Continuous recirculation of the nutrient medium as just described will eventually lead to a depletion of nutrients and a buildup of waste products. New medium must be added and old nutrient medium removed in order to maintain the bioreactor in equilibrium. The old nutrient medium cannot be simply drained off and new nutrient medium added because even the best artificial nutrient medium is a drastic shock to cells when added fresh. This would adversely affect the health of the cells, killing many, and reduce production of products.

Any nutrient medium used in cell culture is conditioned by the cells to make it more acceptable to them. It is therefore necessary to limit the influx of new nutrient medium to a gradual rate, preferably continuously, depending on the needs of the specific cell line being cultured. Medium also must be withdrawn from the system, whether continuously or intermittantly, to maintain an appropriate, relatively uniform volume and also to harvest the bioreactor products. Two possibilities for feeding the new nutrient medium into the system and bleeding old nutrient medium from the system are to have two separate pumps or a single, two-sided pump. Neither of these is satisfactory for a bioreactor which must operate over long periods of time. Slight differences in pumping volume are always present and result in detrimental volume changes with time.

The bioreactor of the present invention solves this problem of maintaining a relatively constant volume by adding a third sensor 34 to the circulation system. Sensor 34 is located in nutrient medium reservoir 9 above sensor 33, and works in conjunction with sensor 32. A pump 36 will feed new nutrient medium into the circulation continuously. When sensor 32 and sensor 34 both sense liquid in the reservoirs at the same time, the bleed pump 35 is activated. The bleed pump 35 removes nutrient medium from the system at a faster rate than it is being added until sensor 32 and sensor 34 no longer simultaneously sense liquid in the reservoirs. At this time the bleed pump 35 is shut off and the medium volume begins to increase again. The positioning of the sensors is determined to maintain the total volume within acceptable limits. Pumping rates are set to limit new nutrient medium input to an acceptable percentage of the total volume per hour and can be adjusted to meet the needs of each cell line.

The pumping system defined by these elements serves to provide a number of particular advantages to the present overall system:

The pumping action does not impose any large shear forces on the nutrient; this functions to conserve the higher molecular weight proteins and the like in the nutrient, which can be degraded by shearing forces. Inasmuch as these are generally the most expensive components of the nutrients, avoiding denaturing shear forces is a highly desirable trait.

The two reservoirs can be made of sufficient size that the increments of fresh make-up nutrient added to the system is a relatively modest proportion of the total amount in the system, thus avoiding shock to the cells from contact with substantial amounts of unconditioned fresh material.

By the nature of its operation the pumping system inherently perfroms automated real time measuring and metering functions to be used as the basis for determining the rate of product recovery and waste removal, the rate of nutrient replacement, and otherwise stabilizing the operation of the system. Highly stable living conditions for the cells results.

The pump structure is such that most conceivable breakdowns do not lead to a loss of sterility.

There is only one active moving mechanical part, the solenoid valve 3 so that the system has exceptional reliability.

When breakdowns do occur, they will most likely be in the air source which powers the operation of the pumping system; it is easy to isolate the rest of the system for repairs or maintenance. "Factory air" is generally suitable for use, given that it will be sterilized as a part of the pumping system. Such air supplies are particularly attractive for their economy, reliability, ease of maintenance, and their general familiarity to most plant personnel.

By its nature the pump can be scaled to any required size and capacity to serve the requirements of the bioreactor system. Larger components are all that is required.

The system is assembled of simple components of very low cost; particularly in larger sizes, the system of the present invention presents very great economies when compared to other types of pumping systems and controls.

Sterile conditions are simple and convenient to establish and maintain in the system with high reliability. In small sizes, the plumbing for the system is so inexpensive that it is even practical to discard old materials to eliminate the cleaning requirements.

For reasons of cost effectiveness, convenience, and sterility, it would be preferable to have a single nutrient medium production unit to supply several bioreactor units containing either the same or different cell lines. To facilitate adding or removing reactor units from the nutrient medium unit and also to prevent any cross contamination, an aseptic break in the system is desirable.

Figure 2A:
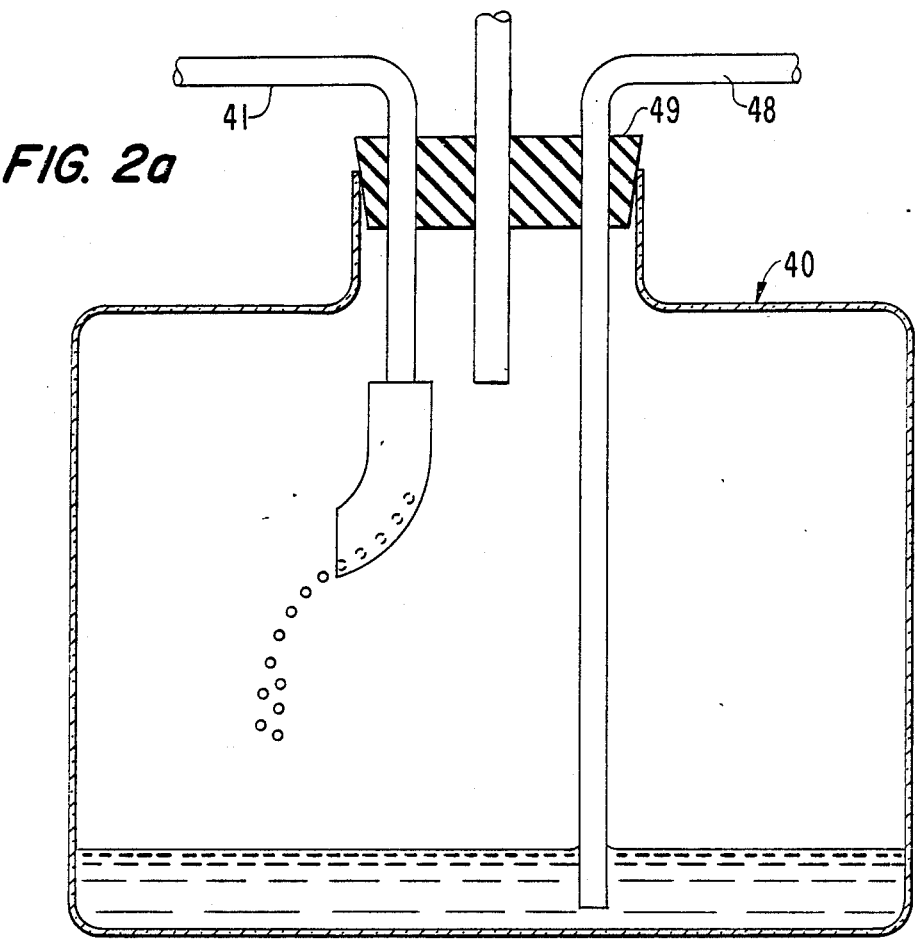
FIGS. 2a and 2b, are a cross sectional view showing the aseptic breaks used in the nutrient medium circulation system.
Figure 2B:
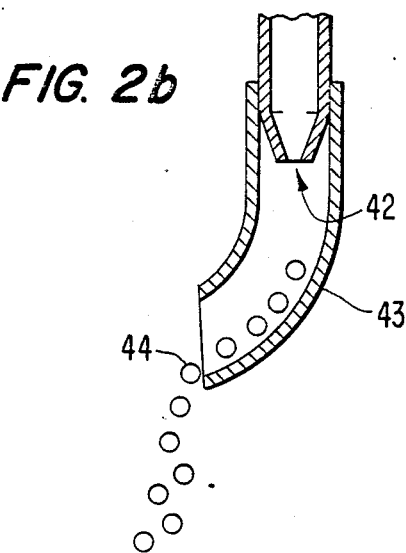

An in-line 0.2 μm filter (or pair of filters) would constitute such an aseptic break, but filters would clog in time, and need periodic replacement. The bioreactor of the present invention uses an alternative device which provides an actual physical break in the liquid flow. This advice, which is employed in the present invention for all the liquid aseptic breaks in use in the system, is shown in detail in FIG. 2:

Liquid flows via inlet line 41 into bottle 40. Line 41 ends in a capillary tip 42. This tip 42 is enclosed by teflon tubing 43 which curves to one side. The liquid flow is regulated so that separate droplets 44 are released from the capillary tip 42, fall to the wall of the teflon tubing 43, roll down its side to the end and drip into the bottle. Since teflon does not wet, the droplets roll separately down the side of the tubing and a bacterial contamination cannot be passed up the tube, even if it should reach the end of the teflon tube through splashing of the drops into the bottle.

At startup, air from air source, at vent 47, which is sterilized by passing it through a 0.2 μm hydrophobic filter 46, is used to pressurize the bottle 40 sufficiently to keep the liquid surface at a low level. The exit tube 48 begins at the bottom of the bottle 40 and passes out the stopper 49. Liquid is forced out through the exit tube 48 by the increase in pressure initially imposed from the air source 47 and thereafter, with valve 45 closed, by the increase created by the incoming volume of the liquid. Generally, two of these aseptic break units are used in series.

Turning again to FIG. 1, the desired gas mixture for aeration of bioreactor core 23 comes from a sterile gas supply (not shown) and passes through bioreactor core 23 via inlet 24 and outlet 25. The bioreactor is seeded with cells suspended in nutrient medium via inlet 21, as described infra.

Cellular metabolism in a bioreactor consumes nutrients and produces the desired products and also wastes. To maintain the dynamic equilibrium of the bioreactor and to harvest its commercial products, nutrient medium must be added to and bled from the system. It is generally preferred to add nutrient make up, from a reservoir, not shown, through aseptic breaks 19 and 20, via line 26 by operation of feed pump 36. The bleeding process, as mentioned previously, accomplishes the functions of maintaining bioreactor medium volume, harvesting products, and removing wastes. If the nutrient medium is inexpensive or all components are depleted simultaneously, it can merely be bled off to a reservoir in a cold room for concentration and purification of product. However, if the nutrient medium contains some expensive components, as is normally the case, a system can be employed to conserve and recirculate these expensive ingredients in particular.

One such system is a tangential flow ultrafiltration module 16 with a 5–100K molecular weight cutoff, preferably as large as possible while still retaining product and growth factors. The nutrient medium feed line 17 enters the ultrafiltration module 16 and the medium flows tangentially across the membrane, out the exit port, and back into the bioreactor circulation. In the process, water and small molecular and ionic components of the nutrient medium flow through the ultrafiltration membrane, are removed via permeate removal line 50 and are pumped away via valve 52, pump 35, valve 53, and via line 55, through aseptic breaks 56, and 57, to waste 59 via discharge line 58. Proteins in the nutrient medium, such as serum albumin, growth factors, and antibodies cannot pass through the ultrafiltration membrane and so remain in circulation. Under this condition, nutrient medium components which would be concentrated by continuous addition, i.e. those with a molecular weight greater than the effective membrane cutoff, are no longer added to the incoming nutrient medium. These components are simply allowed to circulate until their effectiveness wanes. Secreted cellular protein products, such as anitbodies, continuously accumulate. Most cellular waste products are filtered out by the ultrafiltration module.

Even the long-lived nutrient medium components must be replenised eventually and the product must be harvested. The exit line 51 and the permeate line 50 from the ultrafiltration module 16, all shown in FIG. 1, are connected by a valve 52. For harvesting, which may be continuous or intermittant, the valve 52 is opened to line 51, thus bypassing the operation of ultrafilter 16 while valve 53 is opened to line 54 and closed to line 53 and the nutrient medium containing the cellular products is pumped through line 54 into the product concentration circuit. After the maximum allowable amount of medium is bled from the system, the valve 36 is closed so the ultrafiltration module 37 is again working and appropriate amounts of expensive fetal calf serum, fresh growth factors, other hormones, etc. are again added to the incoming nutrient medium. The diverted nutrient medium, containing products, can then be treated to concentrate the high molecular weight products, and separate them from the low molecular weight wastes, by the following procedure:

The stream removed from the bioreactor circuit as described, through line 54, is passed through a first ultrafiltration unit 60. The low molecular weight permeate is removed from the system, via line 64, aseptic breaks 65, 66 and then to waste 59. The remaining stream of partially concentrated high molecular weight materials is provided with a surge buffer via line 61 to surge tank 62, where the stream is reinjected by pump 63 into line 54. The exit line from the first ultrafilter 60 is pumped, by pump 67, via line 68, to a second ultrafilter 70. The permeate from the second ultrafilter 70 passes via line 71 through aseptic breaks 65, 66, to waste 59. The product exiting ultrafilter 70, via line 72, is provided with a second surge line 73, provided with surge tank 74, where the excess volume is recirculated via pump 75 to line 68. The concentrate in line 72 is pumped by pump 76 through aseptic breaks 77, 78 to concentrate collector vessel 80.

The components of the process stream are concentrated from their initial concentration in the process stream to about 100 times the initial levels, while the low molecular weight components are substantially completely removed by the ultrafiltration operations. As those of ordinary skill in the art will recognize, the product will be mixed with the remaining increments of high molecular weight constituents of the nutrient, and will require additional isolation and purification to recover the product in purified form. Such operations are well known to those of ordinary skill in the art, and any known procedure appropriate to the specific product can be employed.

The nutrient feed may be intermittant or continuous. Continuous operation is generally preferred to minimize the shock to the cells of the additions of large amounts of unconditioned nutrient in surges. The bleeding operation may be intermittant, or continuous, and may involve the part-time employment of the ultrafilter 16, alternated with the by-passing of this fractional bleeding operation in favor of removal of an increment of the total stream for product recovery. By balancing of the feed and bleed operations, and controlling the nutrient make-up accordingly, the system can be balanced to conditions most effective for the continuous vitality and productivity of the cells. The particular conditions most conducive to the cultivation will be readily determined in light of the particular behavior of the specific cell line in the reactor. Since it is the low molecular weight constituents of the nutrient which are most rapidly depleted, and the higher molecular weight components are generally the most expensive, balancing of the feed and bleed operations functions to conserve in the system the expensive, slowly depleted components, while relatively rapidly or continuously removing low molecular weight wastes. Considerable economies of operation are attained in this fashion.

The present invention includes four embodiments shown schematically in FIGS. 3, 4, 5, and 6, which allow for the incorporation of an oxygen exchange system, separate from the nutrient medium, into the bioreactor core composed of microporous and/or ultrafiltration membranes. The concept behind the use of the direct, compartmentalized gas exchange chamber is that a moderate, low pressure flow of air or other oxygen-rich gas mixture will provide maximal oxygenation of the cells, while permitting a much slower flow of nutrient medium. The result is the efficient and economical use of the expensive nutrient medium, an overall reduction in bioreactor size, reduced medium flow rates, and greater ease in maintaining sterility. These gas exchange compartment designs can be incorporated into either a stack arrangement or a spiral-wound membrane arrangement.

It is helpful to consider how much advantage will be gained by the incorporation of a separate air chamber into a bioreactor. Hybridoma cell lines vary greatly in their rates of monoclonal antibody production. Based on current knowledge, however, it may be estimated that a bioreactor that produces 1.0 g of antibody per day will need to contain about $10^{11}$ cells. Under traditional culture conditions, with glucose as the sole energy source, hybridoma cells will convert about one half of this glucose into lactate, a process that requires no oxygen. Many attempts have been made to minimize this anaerobic metabolic pathway in hybridoma cells, success at which increases cellular oxygen requirements.

A reasonable estimate based on data and literature values is that cultured hybridoma cells consume about 2.5 picomoles (pmol) of glucose per cell per day. Using this value, $10^{11}$ cells would consume 250 millimoles (mmol) of glucose per day. If only one half is metabolized aerobically, which requires six molecules of oxygen per molecule of glucose, then the oxygen requirement for $10^{11}$ cells is 750 mmol of oxygen per day.

In a bioreactor which delivers oxygen via nutrient medium saturated with air, the concentration of dissolved oxygen at 37° C. is about 0.2 millimolar (mM). The biochemistry of oxygen binding in cultured cells dictates that only about 50% of the dissolved oxygen is available for use. This means that the oxygen concentration of media at 37° C. is effectively only 0.1 mM. At this concentration 7,500 liters of media would need to circulate daily to meet the oxygen requirements of a 1.0 g antibidy per day bioreactor. This dictates a flow rate of 5 liters/min. to support $10^{11}$ cells.

If the nutrient medium flow rate requirement is now considered from the perspective of meeting the glucose requirement of $10^{11}$ cells, a different value is obtained. Glucose supplied at a concentration of 20 mM in nutrient medium is fully adequate to meet cellular needs. Assuming that the glucose is depleted 50% by the cells, its effective concentration is 10 mM. In the previous calculation it was estimated that $10^{11}$ cells would require 250 mmol of glucose per day (the entire aerobic and anaerobic requirement must be considered here). At an effective concentration of 10 mM glucose, 25 liters of nutrient medium would need to circulate per day or 0.02 liter/min.

This example estimates that in a bioreactor which supplies oxygen via the nutrient medium, well over 100 times as much medium must circulate to meet the oxygen requirements of the cells as is needed to meed the nutrient, i.e. glucose, requirements. The use of pure oxygen to saturate the nutrient medium could theoretically produce a 5 fold increase in the dissolved oxygen concentration and thus a 5 fold reduction in nutrient medium flow requirements. However the use of pure oxygen for this purpose creates other problems which makes its use untenable. A gas mixture, such as air, which is about 20% oxygen, appears to be most efficacious and economical. The use of alternate energy substrates, cell lines selected for high production, and other refinements will increase the demand for oxygen in relation to nutrient medium supply. A bioreactor designed with compartmentalized gas exchange chambers can thus be expected to give an advantage of more than two orders of magnitude reduction in nutrient medium flow rates over dissolved gas bioreactors. The economic value of incorporating a separate air chamber into bioreactor design is obvious. Structurally there are several options available.

Figure 3:
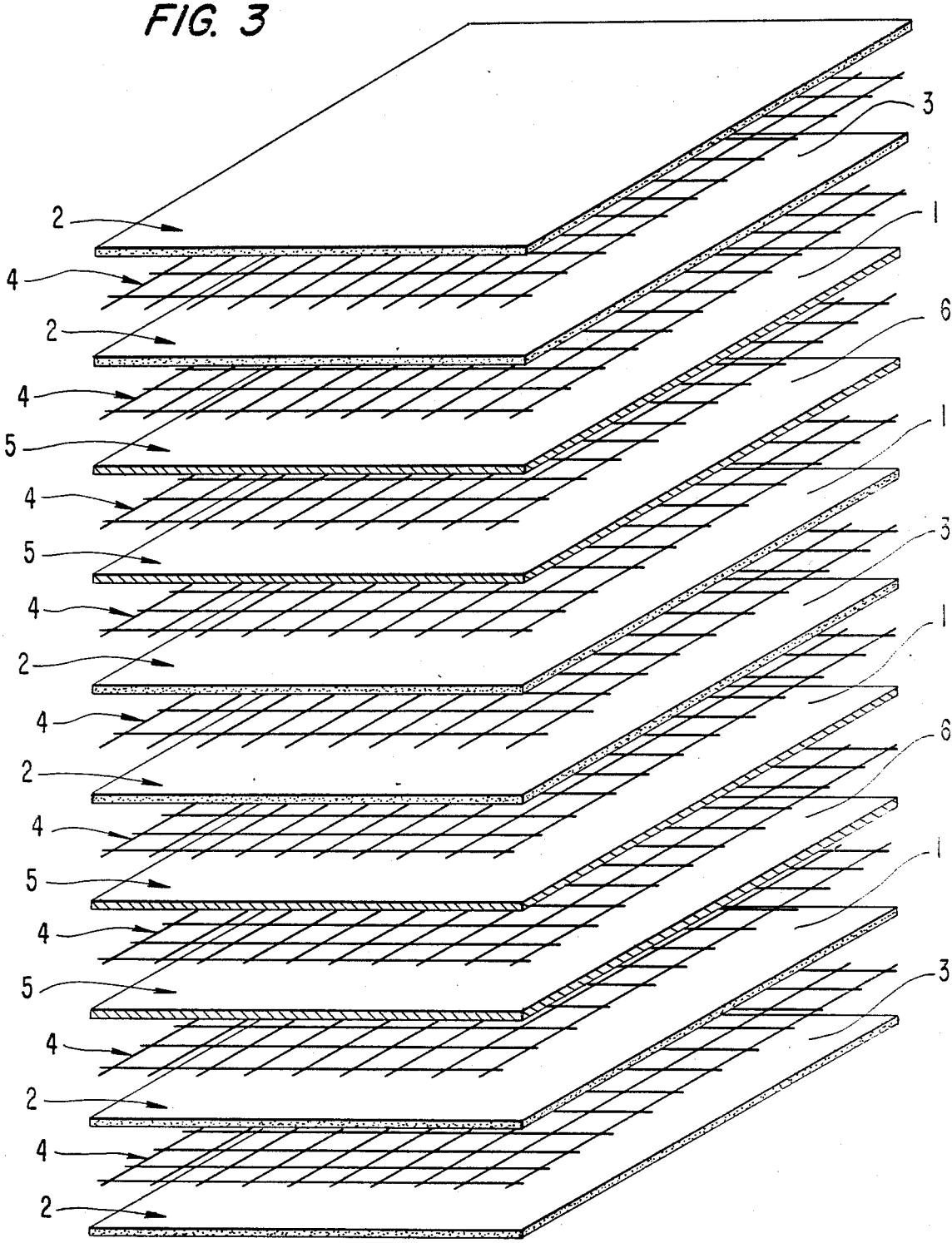
FIG. 3 is an exploded schematic diagram showing the membrane, spacer and chamber arrangement of a bioreactor core for one embodiment of the present invention.

The first of the four embodiments illustrated in FIG. 3, is a multiple layer stacked membrane design. The basic bioreactor core consists of a multilayered series of alternating cell chambers, nutrient medium flow chambers, and gas exchange chambers. The gas exchange chambers are interleaved between two cell chambers, while the nutrient medium flow chambers are located as shown in FIG. 3. Air or another appropriate gas mixture would be passed directly through the inter-membrane space of the gas exchange chambers. To accomplish this, the membranes which form the boundaries between cell chambers and gas exchange chambers would have to be ultraporous, hydrophobic membranes. This type of membrane would not allow the nutrient medium to pass through, but would allow excellent diffusion of oxygen to the cells and diffusion of $CO_2$ away from the cells.

The membranes which form the boundaries between cell chambers and nutrient medium flow chambers are microporous, hydrophilic membranes, normally separated by spacer screens.

This simplest bioreactor core with an internal gas exchange chamber would therefore be constructed, as shown in FIG. 3, by layering materials in the following sequence: hydrophilic membrane 2, spacer screen 4, hydrophilic membrane 2, spacer screen 4, hydrophobic membrane 5, spacer screen 4, hydrophobic membrane 5, spacer screen 4. This sequence is repeated until the desired number of layers is achieved. The result is to create chambers in the following order through the bioreactor core: nutrient medium 3, cell 1, gas 6, cell 1, nutrient medium 3, cell 1, gas 6, cell 1, nutrient medium 3, and so forth. Thus, each cell space 1 will receive nutrients and discharge products and soluble wastes from one side (3), while receiving oxygen and discharging carbon dioxide from the other side (6). Each nutrient medium flow chamber 3 and each gas exchange chamber 6 would supply two cell chambers 1.

Figure 4:
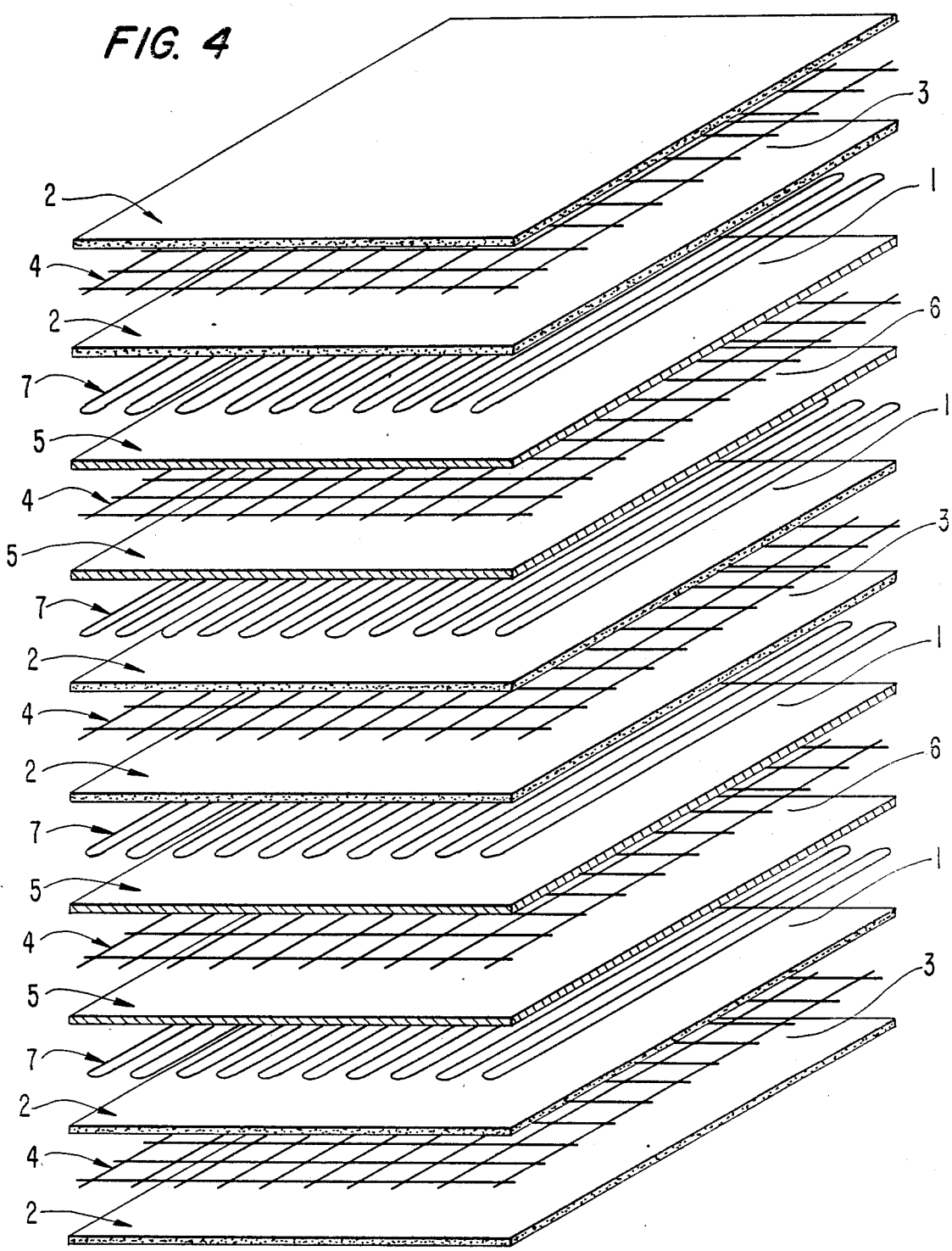
FIG. 4 is an exploded schematic diagram showing another embodiment of the membrane and chamber arrangement of a bioreactor core. In this embodiment the solid fiber spacer screen in the cell chamber is replaced by a hollow fiber spacer screen.

A variation of this simplest embodiment of the bioreactor core is shown in FIG. 4. This second embodiment retains the same membrane and chamber organization as in the first embodiment, but makes a modification in the cell chamber spacer screen to enhance gas exchange. This second embodiment results in the replacement of the solid fiber spacer screen with a screen composed of ultraporous, hydrophobic hollow fibers, sealed at the ends. The bioreactor core is constructed by layering materials in the following sequence: hydrophilic membrane 2, solid fiber spacer screen 4, hydrophilic membrane 2, hollow fiber spacer screen 7, hydrophobic membrane 5, solid fiber spacer screen 4, hydrophobic membrane 5, solid fiber spacer screen 4. This sequence is repeated until the desired number of layers is achieved. The result is to create chambers in the following order through the bioreactor core: nutrient medium 3, cell 1, gas 6, cell 1, nutrient medium 3, cell 1, gas 6, cell 1, nutrient medium 3, and so forth. This new hollow fiber spacer screen 7 would still provide proper spacing of the membranes through the use of appropriately sized fibers, assure the adequate proximity of each cell in the chamber to an oxygen transport surface, and also greatly increase the surface area for gas exchange. This latter function would be accomplished because the hollow fiber screen 7 would be in contact with the hydrophobic membrane 5 of the gas exchange chamber 6, thus allowing rapid diffusion of oxygen into and carbon dioxide into, through and out of the lumina of the hollow fibers 7. While the surface area available for gas exchange through the hydrophobic membrane sheet in both the first embodiment and the second embodiment would be identical, in the second embodiment, the surface area for gas exchange would be increased over that in the first embodiment by the surface area of the spacer screen. This variation on the gas exchange chamber design therefore greatly increases the surface area for gas exchange, and adds the increased gas exchange area within the depth of the cell reaction zone, with the result that wider cell chambers can be used. Wider cell chambers hold more cells and thus reduce the size of the bioreactor, since additional layers of nutrient medium and gas exchange chambers are not necessary to support the additional cells.

Figure 5:
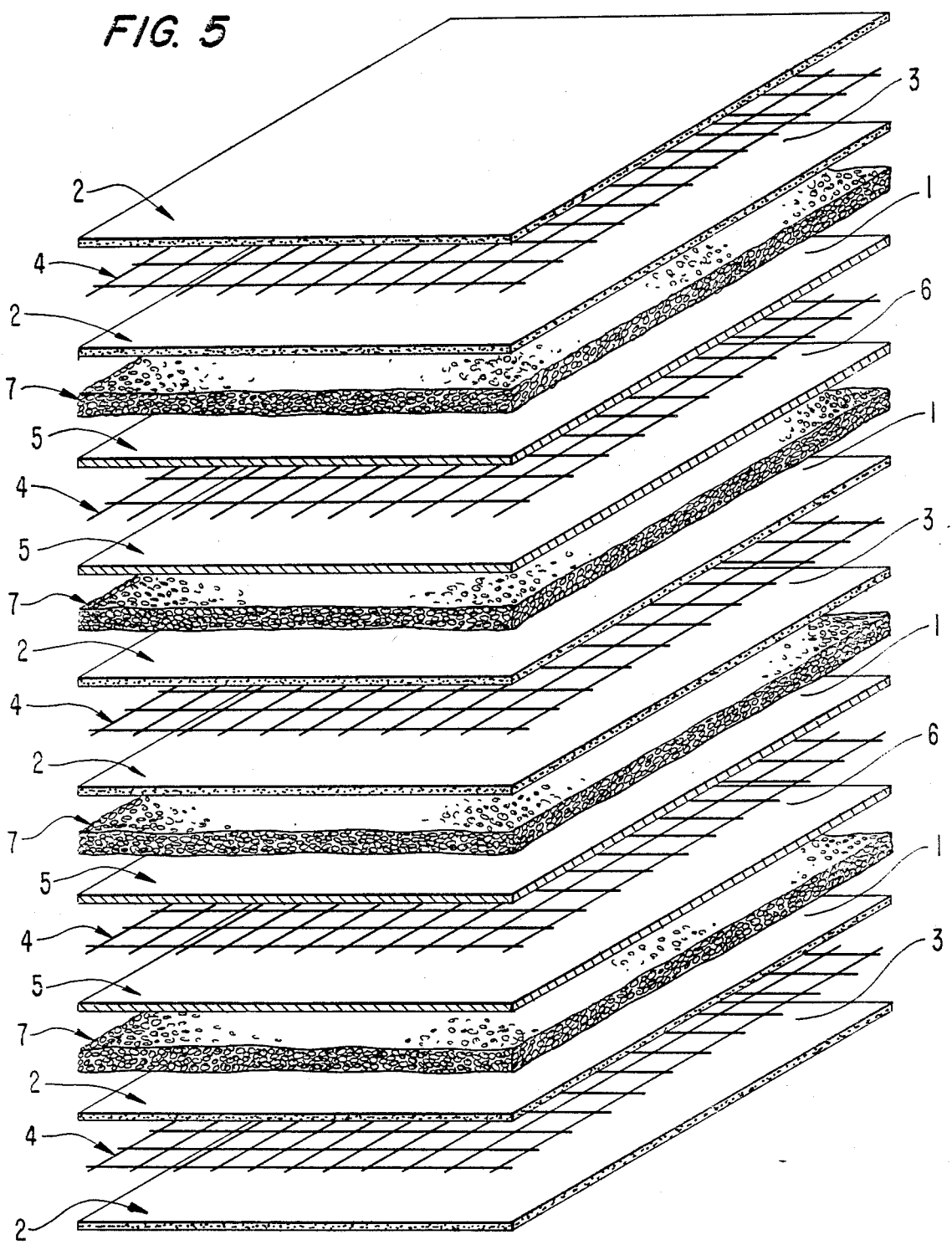
FIG. 5 is a cross-sectional diagram showing another embodiment of the membrane and chamber arrangement of a bioreactor core. In this embodiment the solid fiber spacer screen in the cell chamber is supplemented by particular support material.

Another variation of the simplest embodiment of the bioreactor core is shown in FIG. 5. This third embodiment retains the same membrane and chamber organization as in the first embodiment, but makes a modification in the cell chamber spacer screen to enhance cell attachment. This third embodiment results in the supplementation or replacement of the solid fiber spacer screen with suitable particulate support material for attachment dependent cells. The bioreactor core is constructed by layering materials in the following sequence: hydrophilic membrane 2, solid fiber spacer screen 4, hydrophilic membrane 2, particulate support material 7, with or without a spacer screen, hydrophobic membrane 5, solid fiber spacer screen 4. This sequence is repeated until the desired number of layers is achieved. The result is to create chambers in the following order through the bioreactor core: nutrient medium 3, cell 1, gas 6, cell 1, nutrient medium 3, cell 1, gas 6, cell 1, nutrient medium 3, and so forth. The particulate support material 7 would still provide proper spacing of the membranes through the use of appropriate amounts of material, and also greatly increase the surface area for cell attachment. This second function is especially useful for culturing attachment dependent cells by providing surface area to which the cells may attach.

Figure 6:
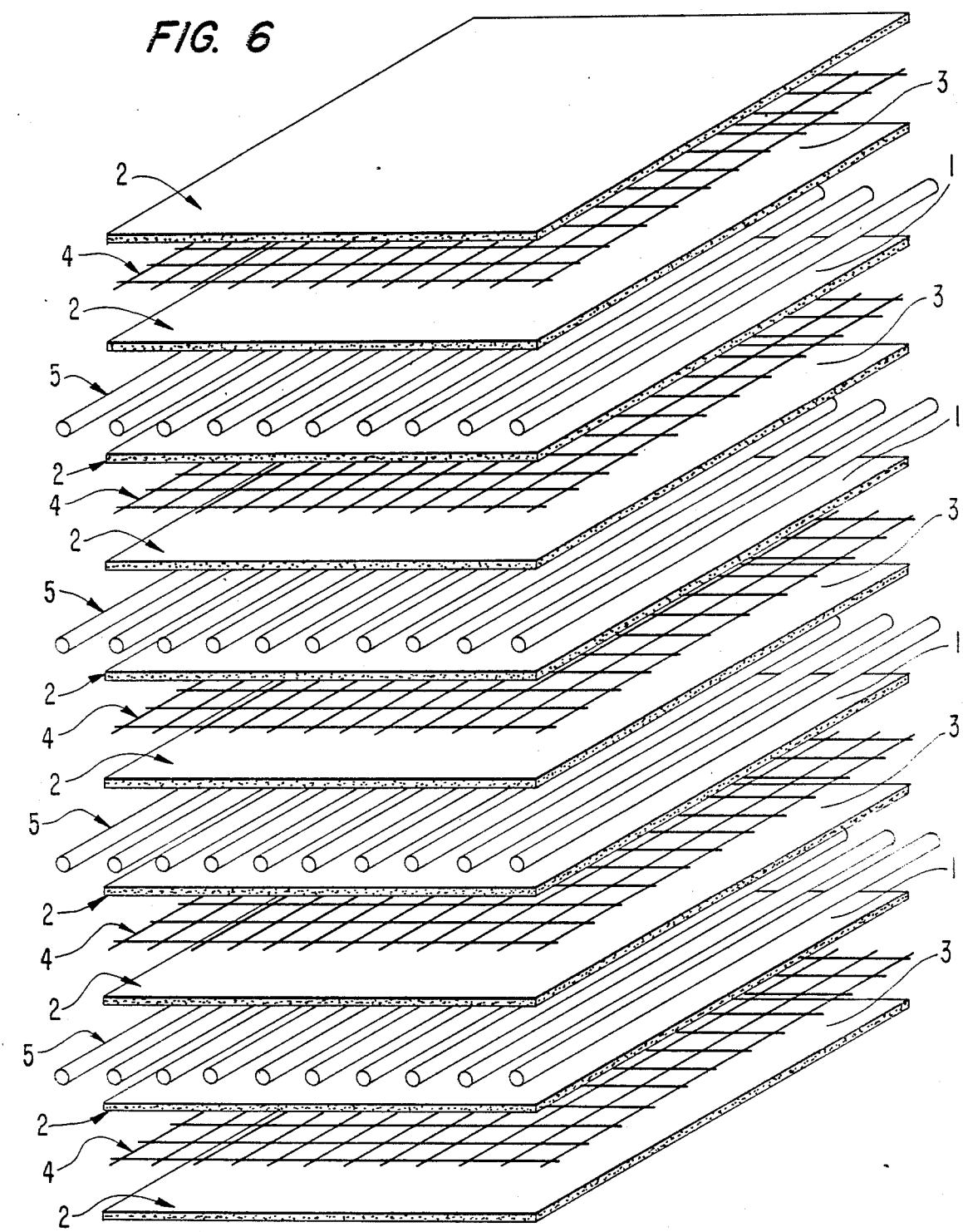
FIG. 6 is a perspective diagram showing another embodiment of the membrane and chamber arrangement of a bioreactor core for a bioreactor having directly fed hollow fibers for gas exchange as part of the bioreactor core.

Another embodiment of the gas exchange chamber design is considerably diffeent from the first three embodiments. This fourth design utilizes alternate cell and nutrient medium chambers separated by hydrophilic membranes, as shown in FIG. 6. The cell chamber spacer screen, found in the simplest embodiment, is replaced by a layer of hydrophobic hollow fibers 5, which can be cross laid with closed ended hollow fibers. The bioreactor core is constructed by layering materials in the following sequence: hydrophilic membrane 2, spacer screen 4, hydrophilic membrane 2, hollow fibers 5, hydrophilic membrane 2, spacer screen 4, hydrophilic membrane 2, hollow fibers 5. This sequence is repeated until the desired number of layers is achieved. The result is to create chambers in the following order through the bioreactor core: nutrient medium 3, cell 1, nutrient medium 3, cell 1, and so forth. The hollow fibers 5 maintain cell chamber 1 spacing, but extend from both sides of the membrane stack where they are gathered into a manifold (not shown in FIG. 6). Air or the desired gas mixture is then pumped through the lumina of the hollow fibers and gas exchange can occur over the entire surface area of the fibers. While this arrangement is highly effective in operation, the difficulties of manifolding the hollow fiber membranes are considerable, and this embodiment is generally less preferred for that reason.

All four of these compartmentalized gas exchange chamber embodiments provide for a much more rapid delivery of oxygen and removal of excess carbon dioxide than do designs where gases must travel dissolved in the nutrient medium. The nutrient medium may also be pumped at a much reduced rate which reflects the nutrient needs of the cells rather than their oxygen needs. Any of these four embodiments described herein may be incorporated into either of two bioreactor core configurations, namely a stack arrangement or a spiral wound arrangement.

The first arrangement of the elements of the bioreactor is referred to herein as the stack. This particular approach utilizes layers of the appropriate membranes, each separated from its adjacent neighbors by a separator, which are sealed in the appropriate arrangements to constitute the various zones and chambers of the reactor. The stack is confined and contained within a reactor vessel or container (for convenience referred to as the "cube", although it should be understood that the shape can be any tetragon, and need not be a cube per se) which is configured to receive the stack and provide manifolding for the supply to the various reactor chambers their respective input and to collect and provide for removal of the outputs. The manifolds are disposed in the following fashion: the seeding ports are preferably disposed along the four opposed edges of the cube normal to the plane in which the membrane sheet slie. Two opposed faces of the cube parallel to the membranes are not employed as manifolds. Of the remaining faces, each opposed pair serves as a bound of a manifold volume for a flow stream, either nutrient or oxygen. On one face, the medium is input to the reactor, while on the opposing face, the output of that stream from the reactor is withdrawn.

In order to provide the means for transport of the nutrient and air or other oxygen source into, through and out of their respective chambers, each chamber is open to a manifold. This objective is conveniently achieved by sealing two opposite sides of each chamber, leaving the other edges open to the manifold in the cube appropriate for that chamber. Each cell chamber is ported into the corner seeding manifold, each air chamber is ported into the air manifold, and the nutrient chambers are ported into the nutrient manifold. The corners of the membranes are sealed into the corners of the cube. The boundaries between the seeding and air manifolds are sealed to the corresponding sides of the cube. The various seals preclude the various manifolds and the various chambers from communicating with those of different kinds. After the reactor is seeded, the seeding manifold and its associated ports into the cell reaction zone are preferably sealed, since they will ordinarily not have further use.

Each manifold is ported to the appropriate input or output lines of the system, as illustrated in FIG. 1.

In practice, the stack is made up, and then placed into the cube, and then is sealed in place, and is ready for use.

Making up of the stack will generally follow the following procedure, which is described with particular reference to the embodiment previously illustrated in FIG. 4, employing a separate air chamber and closed lengths of hollow fiber membranes as the cell separator, and with seeding occuring via the corner manifolds of the cube:

First, a hydrophilic membrane, the inert, woven dacron separator, and a second hydrophilic membrane, each of a width appropriate to the dimensions of the cube and of running length convenient to the user, are stacked with the separator in the center, and sealed by an adhesive along the edges. The running length is then cut transversely across the face of the "sandwich" at appropriate intervals to correspond to the dimensions required of the stack, yielding a flat "tubular" construct of dimensions appropriate to fit into the cube, and having open ends. The interior of each of these elements will constitute a medium chamber when the stack is fully assembled and installed in the cube for operation.

Second, a hydrophobic membrane, the dacron separator, and a second hydrophobic membrane, each of a width appropriate to the dimensions of the cube and of running length convenient to the user, are stacked with the separator in the center, and sealed by an adhesive along the edges. The running length is then cut transversely across the face of the "sandwich" at appropriate intervals to correspond to the dimensions required of the stack, yielding a flat "tubular" construct of dimensions appropriate to fit into the cube, and having open ends. The interior of each of these elements will constitute a gas chamber when the stack is fully assembled and installed in the cube for operation.

To complete the stack, the nutrient chambers are interleaved with the air chambers, with the hollow fiber membrane spacer elements disposed therebetween, with the open ends of all the nutrient chambers aligned with one another, and disposed at ninety degrees of the open ends of the alternating air chambers, which are thus all aligned. As the interleaving procedure continues, an appropriate adhesive is applied in excess at the corners, leaving all medium and gas ports open, such that seeding ports can be created by notching the glued areas to a sufficient depth so as to leave at each corner an opening suitable to communicate with the seeding port of the cube. This process forms the cell chambers which will constitute the cell reactor zones of the reactor. This procedure is continued until the appropriate number of chambers has been formed.

Manifolding of the open flow chambers between the membranes is accomplished by placing the stack into the tetragonal box or cube made of inert material and slightly oversized to accommodate the stack loosely on the four sides facing the edges of the membranes, and thus forming manifolds on each side face of the cube. The membrane stack is held in place and the contents of the two sets of chambers are prevented from mixing by sealing with an adhesive material at each manifold boundary and along each top and bottom edge. Ports supply access to each of the four sides of the stack. The open ends of one set of the chambers are joined by one opposed pair of the manifolds and the open ends of the other, alternating, chambers are joined by the other manifold pair. Two different materials, such as nutrient medium and oxygen stream, can then be passed through the appropriate alternating layers of the stack of membranes. The flow of the two different materials will be at right angles to each other, from the inlet port and manifold, through the chamber, and out the outlet manifold and port.

In the structure of the present invention a separate gas exchange chamber is preferably incorporated within the bioreactor core thereby eliminating the need for using the nutrient medium as a gas transport system. The problem with interleaving a separate gas exchange chamber in this bioreactor core structure, as shown in FIGS. 3, 4, and 5, is that all four side faces of the cube, and the four sides of the membrane stack require utilization for three flow streams, with only two axes of flow available. One solution to this problem is to seal the gas exchange chamber membranes along all four sides, except at two or four corners. Manifolds attached to the corners then allow for input and output of one of the flow streams, preferably the cell seeding stream. This arrangement allows one dimension of the membrane layer, and one pair of opposed manifolds, to be used for nutrient medium flow, the other dimension, and the other pair of manifolds, at a right angle to the first, to be used for air flow, and the corners to be used for the initial cell seeding. Since the seeding operation is generally of concern only during reactor start-up, and then ordinarily employs very gentle flow rates and limited volumes, this approach results in preserving the large stack face manifolds for the continuing operations for uniform nutrient and oxygen supply.

Figure 7:
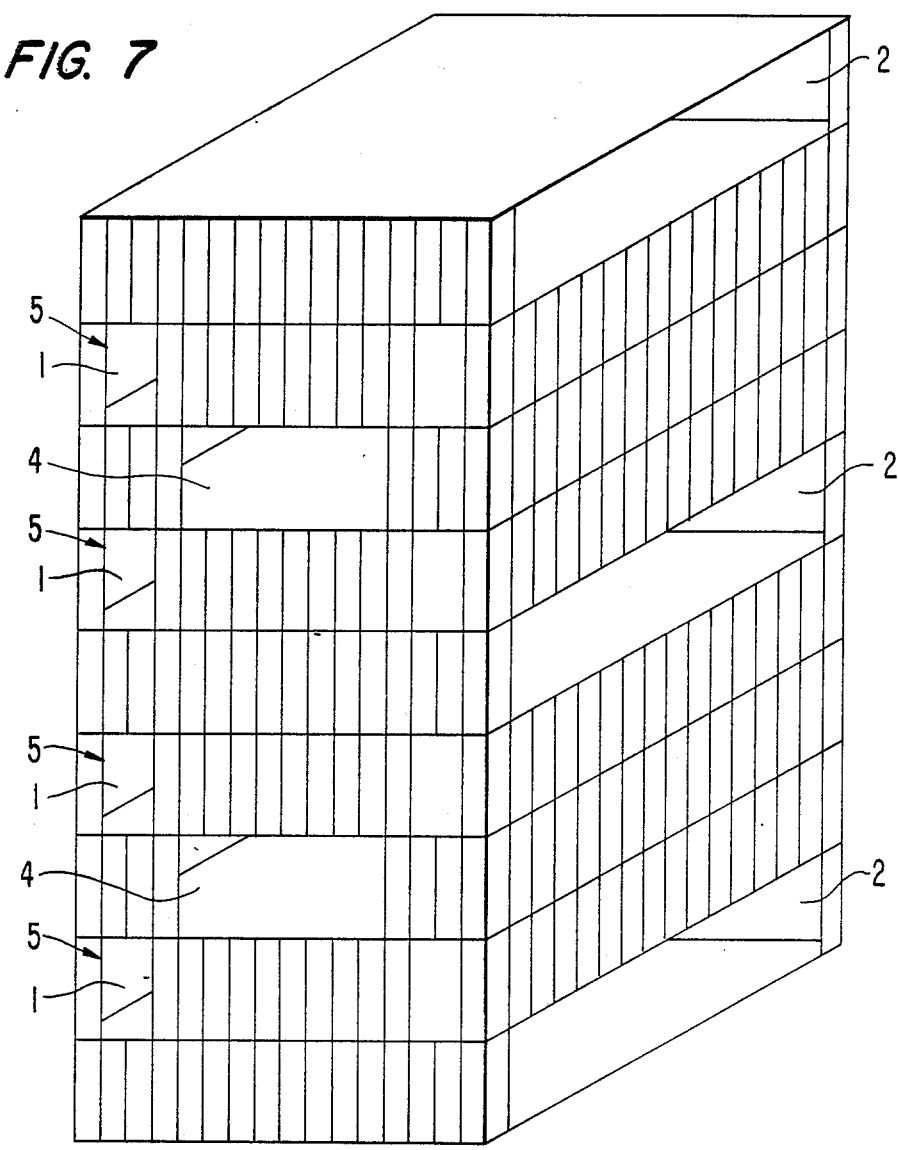
FIG. 7 is a perspective view of a stack bioreactor core for a bioreactor having cell chamber ports at the corners.

To create this embodiment of the stack reactor, square hydrophilic and hydrophobic membranes can be arranged as shown in FIGS. 3, 4, or 5 with either solid fiber or hollow fiber spacer screens, and optionally particulate material, in the cell chambers as described previously in the first three embodiments of the gas exchange chamber. The membranes in this stack of membranes and spacer screens are sealed as shown in FIG. 7. The two hydrophilic membranes enclosinng the nutrient medium chamber 2 are sealed all the way across one side and also on the opposing side. The hydrophobic and hydrophilic membranes enclosing the cell chamber 1 are sealed along all sides except for a small section 5 at the corners on the sides of the nutrient medium chamber seals. The hydrophobic and hydrophilic membranes enclosing the gas exchange chamber 4 are sealed along the entire side of the nutrient medium chamber openings and up to the cell chamber openings 5 along the sides of the nutrient medium chamber seals.

Figure 8:
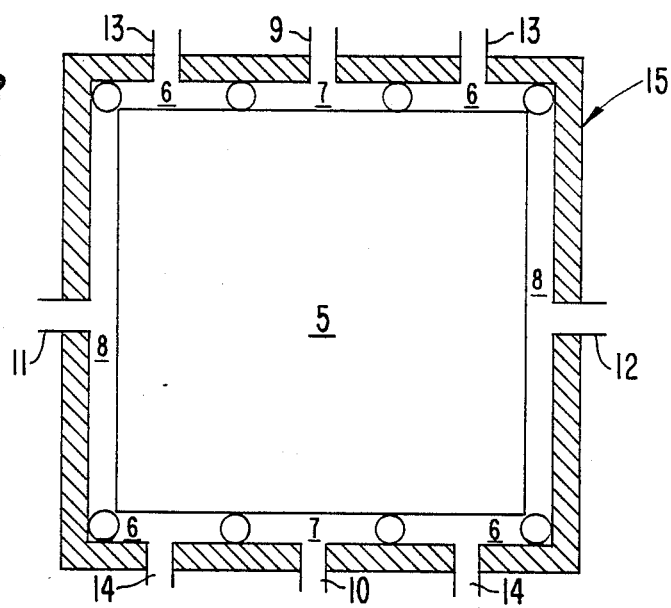
FIG. 8 is a top view of a stack bioreactor core for a bioreactor having cell chamber ports at the corners.

Manifolding of the open flow chambers between the membranes is accomplished by placing the stack into a tetragonal box or cube made of inert material and slightly oversized to accommodate the stack loosely on the four sides as shown in FIG. 8. The membrane stack 5 is held in place and the contents of the three sets of chambers are prevented from mixing by sealing in two places along each edge 15 forming the manifolds 6, 7, and 8, along the bottom, and against the lid which caps the unit. Ports 9, 10, 11, 12, 13 and 14 supply access to each of the four sides and to four of the corners of the stack. All of the cell chamber openings are joined by corner manifolds 6. Manifolds 8 on two opposing sides join the gas exchange chambers while manifolds 7 on the other two opposing sides distribute and collect the nutrient medium flow. When the open ends of the chambers in each dimension are joined by the stack manifolds, cells can be seeded into the cell chambers, via input ports 13, cell chamber manifold 6, the cell chambers in the membrane stack 5, cell chamber manifold 6, and output ports 14, while nutrient medium can be passed through spaces at a right angle to the direction of the seeding flow, via input port 11, nutrient medium chamber manifold 7, the nutrient medium chambers in the membrane stack 5, nutrient medium chamber manifold 7, and output port 12. Gas flows through the gas exchange chambers via input port 9, gas exchange chamber manifold 8, the gas exchange chambers in the membrane stack 5, gas exchange chamber manifold 8, and output port 10. Once seeded, the cell spaces are closed off, while nutrient medium continuously perfuses the cells through the adjacent nutrient medium flow chambers and oxygen and carbon dioxide diffuse from and to the adjacent gas exchange chambers.

In the embodiment of FIG. 6, which employs no separate air or oxygen chamber, the hollow fiber membranes carry the flow of the oxygen source into the cell chamber, and the hollow fibers must be directly manifolded to an air or oxygen supply. In this embodiment, the hollow fibers must have open ends, which pass through the glue lines which close off the edges of the cell chamber to an air or oxygen manifold. Because of the difficulty of forming such an arrangement, this embodiment is not preferred.

Figure 9A:
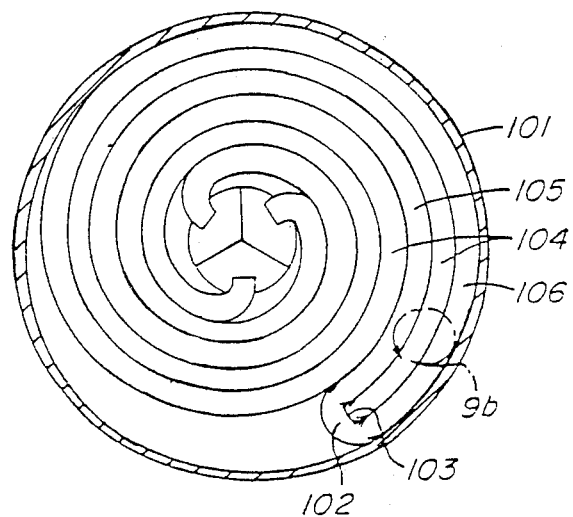
FIG. 9a and FIG. 9b are a schematic detail showing the specific arrangement of the membranes and spacers of each layer of the spiral.
Figure 9B:
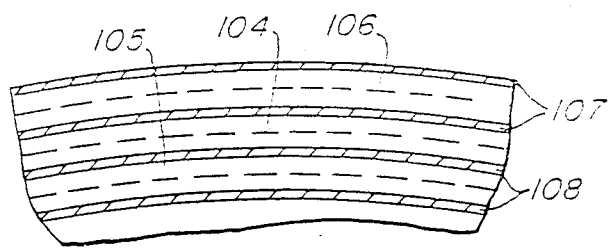
Figure 10A:
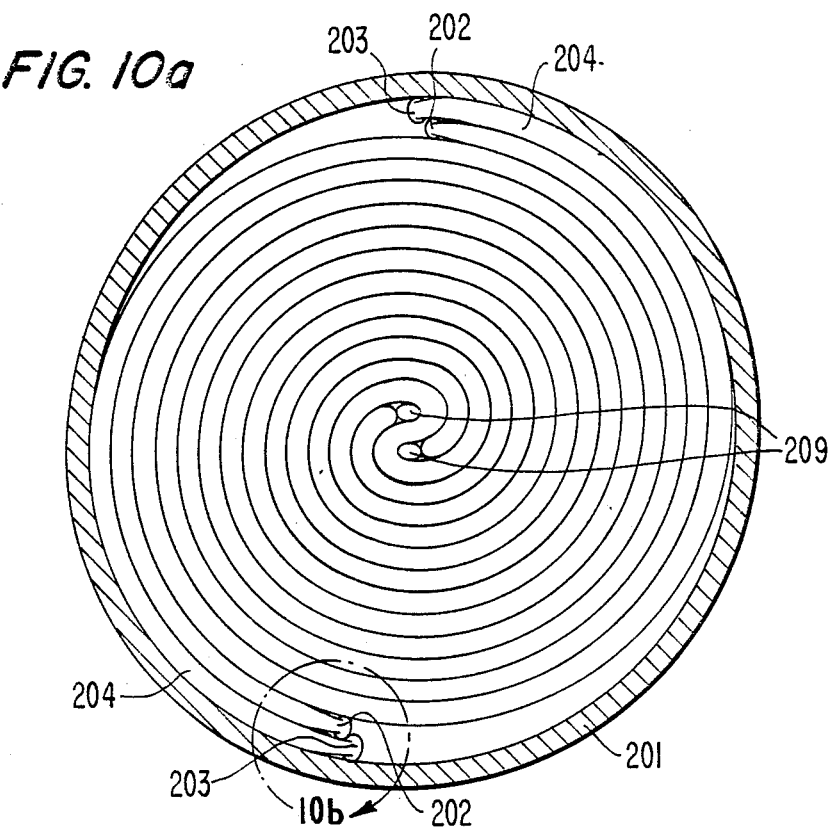
FIG. 10a and FIG. 10b are a schematic detail showing the specific arrangement of the membranes and spacers of each layer of the spiral.
Figure 10B:
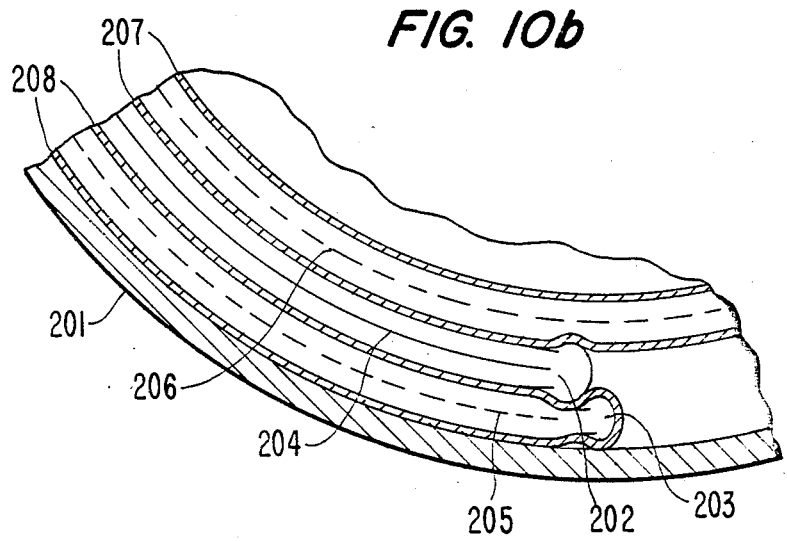

The second arrangement for the bioreactor core organizes the membranes and chamber layers in exactly the same relative configuration, but in a different physical arrangement. Rather than the stacks of membranes of the stack arrangement, in this arrangement the layers of membranes are wound into a spiral. This can be accomplished in either of two manners: (1) the end-wound spiral as shown in FIG. 9 and 9a; or (2) the center-wound spiral, starting the spiral in the middle of the membrane length, with the result that both ends are on the outer perimeter as shown in FIG. 10 and 10a. Any of the three compartmentalized gas exchange chamber embodiments can be organized into a spiral, wound in either manner as can be the simplest embodiment of the present invention.

The end-wound spiral is begun by sealing each chamber into a central manifold. The membranes are then wound around this manifold center until the desired size is achieved, whereupon the outer manifold is sealed into place. It can be seen from FIG. 9 and 9a that the membrane layers form a nutrient medium chamber 106, a cell chamber 104, a gas exchange chamber 105, and another cell chamber 104. The cell chambers 104 are sealed into cell chamber manifolds 102 and the gas exchange chamber 105 is sealed into gas exchange chamber manifolds 103. The gas exchange chamber is of course formed of hydrophobic membranes 108 while the cell chambers and the nutrient medium chamber are formed of hydrophilic membranes 107. The entire spiral is then placed into a container whose outer shell 101 is shown in FIG. 9.

The center-wound spiral is shown in FIG. 10 and 10a and employs a generally double tear drop-shaped spindle 209 about which the membrane layers are wound. At the outer perimeter of the spiral bioreactor there are then two ends to each of the layers. These ends are sealed into manifolds, namely cell chamber manifolds 202, and gas exchange chamber inlet and outlet manifolds 203. The membranes are stacked prior to winding around spindle 209 so that the cell chamber 204 is sandwiched between gas exchange chamber 205 and nutrient medium chamber 206. The entire spiral is then placed into a container whose outer shell 201 is shown in FIG. 10 and 10a.

The spiral-wound constructions shown in FIGS. 9 and 10 have a number of common elements. In each only one repeating unit of membranes is ordinarily used. Each membrane and spacer layer, solid or hollow fiber, is in the form of long strips of the desired width. Where appropriate the layers are sealed along the edges at the point at which the spiral will begin to be wound. Then the edges are sealed, preferably as the layers are wound into a spiral to compensate for the continuing change in spiral circumference which varies independently for each layer. The outer membrane of the first layer becomes the inner membrane of the next layer and so forth until the desired bioreactor diameter is achieved. Cell and gas exchange chambers are continuous along the spiral from the outside to the inside in the end-wound construction shown in FIG. 9 and 9a and from the outside to the inside and back out in the center-wound construction shown in FIG. 10 and 10a.

Once the membranes are wound appropriately and all manifolds are sealed in place, the whole cylinder is slid into a surrounding shell (designated as 101 and 201 in FIGS. 9, and 10) and sealed in place. The ends are then capped, leaving ports for nutrient medium to flow in or out. Again with particular reference to FIG. 9 and 9a, in both spiral constructions the membranes forming the nutrient medium flow chambers are not sealed along their long edges and nutrient medium flows across the layers of the spiral, i.e., in a direction normal to the plane of the Figure, via an input port located in the top closure of the cylinder, into a nutrient medium inlet manifold, through the spiral windings, nutrient medium outlet manifold, and an output port, from one end of the cylinder to the other. These features are commonly known and understood by those of ordinary skill in the art, and are not shown in the drawings. Cell seeding takes place via input port into cell chamber manifolds 102, into the cell chamber and through the hydrophilic membranes and out via the nutrient output port. The cells, which are unable to pass through the membrane are retained in the cell chamber. Gas flows through the spiral via input port to gas exchange chamber inlet menifold 103, through the gas exchange chamber 104, outlet manifold 103, and an output port.

The major difference between the center wound spiral and end wound spiral configurations, as clearly shown in FIG. 10 and 10a, is that the center wound spiral embodiment requires a central spindle, 209, rather than a manifold at the center. All the terminal manifolds are disposed around the outer periphery of the spiral winding, ported through the end cap of the shell structure.

One of the greatest attractions of the spiral wound configurations is the convenience of handling and equipping the system in very convenient fashion. The spiral wound reactor in its cartridge housing can be sealed in sterile condition, stored before use, and easily installed in about the same fasion as employed for handling of cartridge filters. With appropriate adjustments and modifications, the reactor can be used by installation in filter cartridge housings, making the set-up and installation of the system, as well as its use, a convenient and familiar task for many plant personnel.

Spirals can currently be constructed with a diameter of up to about 12 inches and a cylinder length of up to about 3 feet. Such a cylinder would have a total volume of about 21.2 liters which would mean a cell chamber capacity of about 5000 cm$^3$. Correcting for the volume occupied by the spacer screen, the cell space is about 3000 cm$^3$. At $5 \times 10^8$ cells/cm$^3$, such a reactor would contain about $1.5 \times 10^{12}$ cells and produce about 10 g of antibody per day. This is comparable to the production of a 1000 liter batch-type reactor. Many of these spiral units can be employed in parallel to construct a bioreactor of any desired capacity.

In conclusion, this invention relates to layered membrane immobilized cell bioreactors and various designs for compartmentalized gas exchange chambers as applicable to layered membrane immobilized cell bioreactors. The incorporation of compartmentalized gas exchange chambers into a bioreactor provides maximal oxygenation of the cells for greater production of antibodies, while allowing for minimal circulation of nutrient medium for greater efficiency and compactness of design. Economic advantages accrue from the greater metabolic activity of the cells which can manufacture more of the desired products and the reduction in nutrient medium pumping requirements.

The process of colonizing the bioreactor can be accomplished by growing a sufficient number of cells in a traditional tissue culture facility and transferring them to the bioreactor. However, this approach requires that large quantities of sterile media be handled and that considerable incubator space be available to grow the cells. This is a very time consuming and expensive means toward bioreactor start up.

A more practical approach, both in terms of cost and functionality, is to grow a relatively small number of cells with which to seed the bioreactor. Once colonized, the bioreactor is filled to capacity by the subsequent divisions of the cells. Relatively uniform packing of the cells is essential for maximum bioreactor efficiency and productivity. The bioreactor designs of the present invention will result in cell seeding which distributes the cells uniformly within the cell chambers using a self regulatory process.

The microporous membranes of the bioreactor designs of the present invention allow the nutrient medium to pass through while retaining the cells. The two membranes which form the cell chamber are kept uniformly separated by a spacer screen. Thus, when the seed culture is pumped into the cell chamber of the bioreactor the pressure forces the media portion through the microporous membrane into the nutrient medium flow chamber. The cells cannot pass throgh the membrane so are filtered out of the seed culture medium and thus deposited immediately in front of the seeding entry port. These cells reduce medium flow through the membrane in that area. Seed culture now entering the cell chamber passes over the deposited cells to open membrane where the medium can pass through, again filtering out the suspended cells. Cells are thus continuously deposited at the periphery of the ever-expanding monolayer until the membrane is covered.

As the flow of seed culture medium which perfuses the cells begins to slow, the nutrient medium circulation system must begin to operate to provide nutrients and oxygen for the cells. When the cell chamber is completely colonized, the nutrients diffuse from the nutrient medium chamber into the cell chamber. under the proper conditions, the cells then reproduce to substantially fill the reactor zone, with a high population density and thus with high production capacity.

In the context of the present invention, the membranes employed will generally be selected from among those comercially available to the art. A wide variety of both ultraporous, hydrophobic membranes suitable for the gas transfer, and microporous, hydrophilic membranes suitable for the nutrient diffusion, are available from a number of sources.

Spacer screens to be employed in the present invention are generally familiar to the art, and are commercially available in a variety of materials, specific configurations, and dimensions. Conveniently, woven dacron polyester materials of appropriate dimensions may be employed. When it is desired to employ hollow ultraporous membrane hollow fiber spacers, these materials are also available from a number of sources.

Particulate materials suited for use in the cell reactor with attachment dependent cells are also widely known to the art and are generally available.

Nutrients suitable for the cultivation of cells, particularly hybridoma cells, in the context of the present invention are well known. Any nutrient suited for a particular cell line can be employed.

What is claimed is:

1. A cell reactor comprising:
   A. at least one layered cell reactor compartment for confining and retaining living cells and nutrient solution to produce exocellular products,
   B. at least one associated nutrient compartment for feeding liquid cell nutrients to each said cell reactor compartment and for the removal of exocellular products and metabolic wastes from said cell reactor compartment,
   C. each said cell reactor compartment and said associated nutrient compartment having a common boundary formed by a porous hydrophyllic sheet membrane having a pore size adapted to permit flow therethrough by diffusion of nutrient, exocellular products and metabolic wastes, and preventing passage therethrough of cells,
   D. at least one associated gas compartment for the supply of free oxygen into solution in nutrient solution in each said cell reactor compartment,
   E. each said cell reactor compartment and said associated gas compartment having a common boundary formed by an oxygen transport membrane adapted to permit flow therethrough of free oxygen and adapted to prevent flow of cells, nutrient, exocellular products and metabolic wastes into said gas compartment,
   F. each said cell reactor compartment and said associated oxygen transport membrane being disposed so that substantially all cells within said cell reactor compartment are within effective oxygen diffusion distance of up to about 100 micrometers to about 200 micrometers of said oxygen transport membrane, said oxygen diffusion distance being effective to maintain cell viability and cell densities greater than about $5 \times 10^8$ cells per milliliter by transport of dissolved oxygen from said oxygen transport membrane to said cells solely by diffusion; and
   G. each said cell reactor compartment layer is separated from each adjacent cell reactor chamber layer by either (i) a nutrient transport compartment or (ii) a gas compartment on one side and a nutrient transport compartment on an opposite side.

2. The cell reactor of claim 1 wherein each said oxygen transport membrane is a hydrophobic porous membrane having a mean pore size of from about 0.005 to about 1.0 microns and a breakthrough pressure sufficient to prevent flow of liquid from said cell reactor compartment to said gas compartment.

3. The cell reactor of claim 1 wherein a separator means maintains a predetermined thickness of said cell reactor compartment to provide the effective oxygen diffusion distance from said cells.

4. The cell reactor of claim 3 wherein the separator means is a porous web of hydrophobic material inert to the materials within said reactor compartment.

5. The cell reactor of claim 3 wherein the separator means is a layer of hydrophobic hollow fiber membranes having a mean pore size of from about 0.01 to about 0.1 microns and a breakthrough pressure sufficient to prevent transport of liquid from said reactor compartment, said fibers having closed ends and being in gas diffusion contact with said gas compartment and serving as an element thereof.

6. The cell reactor of claim 1 wherein said plurality of cell reactor compartments are disposed in a stack and having each cell reactor compartment separated from each next cell reactor compartment by either (i) a nutrient transport compartment or (ii) a gas compartment on one side and a nutrient transport compartment on an opposite side.

7. The cell reactor of claim 6 wherein said stack is terminated by either a gas compartment or a nutrient transport compartment.

8. The cell reactor of claim 1 wherein (i) each gas compartment is formed of a pair of hydrophobic porous sheet membranes and each pair being maintained a predetermined distance apart by porous separator means and (ii) each nutrient transport chamber is formed of a pair of said hydrophillic membranes and each pair being maintained a predetermined distance apart by porous separator means.

9. The cell reactor of claim 8 wherein each pair of hydrophillic membranes communicates with an inlet manifold on one edge and an outlet manifold on an opposite edge and each pair of hydrophobic membranes communicates with an inlet manifold on one edge and an outlet manifold on an opposite edge, the manifolds for the respective membrane pairs being at ninety degrees to each other.

10. The cell reactor of claim 1 wherein each cell reactor compartment is separated from its next adjacent cell reactor compartments by a nutrient transport compartment on one side and a gas compartment on the opposite side.

11. The cell reactor of claim 1 wherein the cell reactor compartment is in the form of a spiral.

12. The cell reactor of claim 11 including a separator means to maintain a predetermined thickness in said cell reactor compartment.

13. The cell reactor of claim 12 wherein the nutrient compartment is formed by a pair of said hydrophillic membranes and the oxygen transport compartment is formed by a pair of hydrophobic sheet membranes.

14. The cell reactor of claim 12 having (A) each pair of hydrophillic membranes sealed along two opposite edges that are perpendicular to the spiral axis and communicating with an inlet manifold at one open edge and with an outlet manifold along the opposite open edge and (B) each pair of hydrophobic membranes sealed along two opposite edges that are parallel to the spiral axis and communicating with an inlet manifold at one open edge and an outlet manifold along the opposite open edge.

15. The cell reactor of claim 11 wherein said spiral is end wound.

16. The cell reactor of claim 11 wherein said spiral is center wound.

17. The cell reactor of claim 11 whreein said spiral is contained within a cartridge housing.

18. The cell reactor of claim 1 having said oxygen transport membrane in the form of hollow fibers.

19. The cell reactor of claim 18 whrein said nutrient transport compartment is formed by a pair of said hydrophillic membranes which are spaced apart a predetermined distance to provide the effective oxygen diffusion distance for the cells.

20. The cell reactor of claim 19 wherein said spacing is effected by disposing said hollow fibers between said hydrophillic membranes.

21. The cell reactor of claim 19 wherein said spacing is effected by a porous web of material inert to the elements within said cell reactor compartment.

22. The cell reactor of claim 18 having a plurality of said cell reactor compartments and having said compartments disposed in a stack and having each cell reactor compartment separated from each adjacent cell reactor compartment by a commonly shared nutrient transport compartment.

23. The cell reactor of claim 22 wherein said nutrient transport compartments are formed by pairs of said hydrophillic membranes that are maintained at predetermined distances from each other.

24. The cell reactor of claim 23 wherein said distances are effected by porous separator means.

25. The cell reactor of claim 23 wherein said distances are effected by the hollow fibers of the gas compartment.

* * * * *